US011312780B2

United States Patent
Boquet et al.

(10) Patent No.: US 11,312,780 B2
(45) Date of Patent: Apr. 26, 2022

(54) ANTIBODY DIRECTED AGAINST THE ENDOTHELIN RECEPTOR BETA SUB-TYPE

(71) Applicant: COMMISSARIAT À L'ÉNERGIE ATOMIQUE ET AUX ÉNERGIES ALTERNATIVES, Paris (FR)

(72) Inventors: Didier Boquet, Les Pavillons Sous Bois (FR); Frédéric Ducancel, Longjumeau (FR); Amaury Herbet, Courbevoie (FR); Narciso Costa, Saulx les Chartreux (FR); Jean-Philippe Hugnot, Montpellier (FR)

(73) Assignee: COMMISSARIAT À L'ÉNERGIE ATOMIQUE ET AUX ÉNERGIES ALTERNATIVES, Paris (FR)

( * ) Notice: Subject to any disclaimer, the term of this patent is extended or adjusted under 35 U.S.C. 154(b) by 0 days.

(21) Appl. No.: 16/310,655

(22) PCT Filed: Jun. 22, 2017

(86) PCT No.: PCT/EP2017/065442
§ 371 (c)(1),
(2) Date: Dec. 17, 2018

(87) PCT Pub. No.: WO2017/220739
PCT Pub. Date: Dec. 28, 2017

(65) Prior Publication Data
US 2019/0185574 A1 Jun. 20, 2019

(30) Foreign Application Priority Data

Jun. 24, 2016 (FR) .................................... 1655915

(51) Int. Cl.
| | | |
|---|---|---|
| *A61K 39/395* | (2006.01) | |
| *C07K 16/28* | (2006.01) | |
| *C07K 16/30* | (2006.01) | |
| *A61P 35/00* | (2006.01) | |
| *G01N 33/574* | (2006.01) | |
| *A61K 39/00* | (2006.01) | |

(52) U.S. Cl.
CPC .......... *C07K 16/2869* (2013.01); *A61P 35/00* (2018.01); *C07K 16/3053* (2013.01); *G01N 33/57407* (2013.01); *A61K 2039/505* (2013.01); *C07K 2317/24* (2013.01); *C07K 2317/34* (2013.01); *C07K 2317/565* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 4,816,567 A | 3/1989 | Cabilly et al. |
| 2010/0003240 A1 | 1/2010 | Schneider et al. |

FOREIGN PATENT DOCUMENTS

| JP | 2012-111706 A | 6/2012 |
| WO | 2012/045776 A1 | 4/2012 |
| WO | 2013/063001 A1 | 5/2013 |

OTHER PUBLICATIONS

MacCallum et al. (1996). J. Mol. Biol. 262:732-745.*
De Pascalis et al. (2002). Journal of Immunology. 169:3076-3084.*
Casset et al. (2003). Biochemical and Biophysical Reseaerch Communications. 307:198-205.*
Chen et al. (1999). J. Mol. biol. 293:865-881.*
Wu et al. (1999). J. Mol. Biol. 294:151-162.*
Rudikoff et al. (1982). PNAS. 79:1979-1983.*
International Search Report for International Application No. PCT/EP2017/065442, dated Sep. 19, 2017.
Written Opinion for International Application No. PCT/EP2017/065442, dated Sep. 19, 2017.
Preliminary French Search Report for Application No. 1655915, dated Feb. 21, 2017.
R. Shah "Endothelins in health and disease", European Journal of Internal Medicine, vol. 18, 2007, pp. 272-282.
Bagnato et al., "The endothelin axis in cancer", The International Journal of Biochemistry & Cell Biology, vol. 40, 2008, pp. 1443-1451.
Buckanovich et al, "Endothelin B receptor mediates the endothelial barrier to T cell homing to tumors and disables immune therapy", Nature Medicine, vol. 14, No. 1, Jan. 2008, pp. 28-36.
Kondoh et al, "Isolation of anti-endothelin receptor monoclonal antibodies for use in receptor characterization", Biochemical and Biophysical Research Communications, vol. 172, No. 2, 1990, pp. 503-510.
Yamaguchi et al, "Characterization and application of monoclonal antibodies against human endothelin B receptor expressed in insect cells", Biotechnology Letters, vol. 26, 2004, pp. 293-299.
Asundi et al, "An antibody-drug conjugate targeting the endothelin B receptor for the treatment of melanoma", Clinical Cancer Research, vol. 17, Jan. 2011, pp. 965-975.

(Continued)

*Primary Examiner* — Christine J Saoud
*Assistant Examiner* — Jon M Lockard
(74) *Attorney, Agent, or Firm* — Pearne & Gordon LLP

(57) ABSTRACT

Antibodies directed against the endothelin receptor sub-type B, in particular monoclonal antibodies, a fragment or derivative thereof. The present disclosure also relates to the therapeutic, diagnostic use or as a research tool of such an antibody in the field of cancers and in particular glioblastoma.

21 Claims, 6 Drawing Sheets

Specification includes a Sequence Listing.

(56) References Cited

OTHER PUBLICATIONS

Allard et al, "Electroporation-aided DNA immunization generates polyclonal antibodies against the native conformation of human endothelin B receptor", DNA and Cell Biology, vol. 30, No. 9, 2011, pp. 727-737.
M-P Lefranc, "IMGT databases, web resources and tools for immunoglobulin and T cell receptor sequence analysis, http://imgt.cines.fr", Leukemia, vol. 17, 2003, pp. 260-266.
Verhoeyen et al, "Reshaping human antibodies: Grafting an antilysozyme activity", Science, vol. 239, Mar. 1988, pp. 1534-1536.
Vaughan et al, "Human antibodies by design", Nature Biotechnology vol. 16, Jun. 1998, pp. 535-539.
Sambrook et al, "Molecular cloning", 2nd ed., New York: Cold Spring Harbor Laboratory Press, 1989.

* cited by examiner

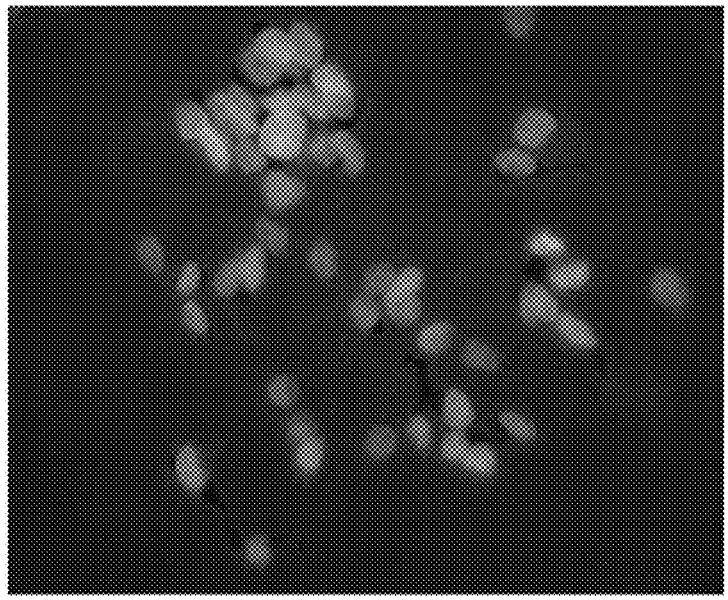

FIG.4

VLRendoMabB49
GATGTTTTGATGACCCAAACTCCACTCTCCCTGCCTGTCAGTCTTGGAGATCAAGCCTCCATCTCTTGCAGATCT
AGTCAGAGCATTGTACATAGTAATGGAAACACCTATTTAGAATGGTACCTGCAGAAACCAGGCCAGTCTCCAAAG
CTCCTGATCTACAAAGTTTCCAACCGATTTTCTGGGGTCCCAGACAGGTTCAGTGGCAGTGGATCAGGGACAGAT
TTCACACTCAAGATCAGCAGAGTGGAGGCTGAGGATCTGGGAGTTTATTACTGCTTTCAAGGTTCACATGTTCCG
TGGACGTTCGGTGGAGGCACCAAGCTGGAAATCAAA VLRendoMabB49
DVLMTQTPLSLPVSLGDQASISCRSSQSIVHSNGNTYLEWYLQKPGQSPKLLIYKVSNRFSGVPDRFSGSGSGTD
FTLKISRVEAEDLGVYYCFQGSHVPWTFGGGTKLEIK

FIG.5A

VHRendoMabB49
CAGGTCCAACTGCAGCAGCCTGGGGCTGCGCTTGTGAAGCCTGGGGCTTCAGTGAAGCTGTCCTGCAAGGCTTCT
GGCTACACCTTCATCAGCTACTGGATGCTCTGGGTGAAGCAGAGGCCTGGACGAGGCCTTGAGTGGATTGGAAGG
ATTGATCCTGATAGCGGTGGTACTAAGTACAATGAGAAGTTCAAGAGCAAGGCCACACTGACTGTAGACAAATCC
TCCAGCACAGCCTACATGCAGCTCAGCAGCCTGACATCTGAGGACTCTGCGGTCTATTATTGTGCAAGAGAAGGG
GATTACGCCTGGTTTGCTTACTGGGGCCAAGGGACTCTGGTCCCTGTCTCTGCA VHRendoMabB49
QVQLQQPGAALVKPGASVKLSCKASGYTFISYWMLWVKQRPGRGLEWIGRIDPDSGGTKYNEKFKSKATLTVDKS
SSTAYMQLSSLTSEDSAVYYCAREGDYAWFAYWGQGTLVPVSA

FIG.5B

VLRendoMabB41
GATGTTTTGATGACCCAAACTCCACTCTCCCTGCCTGTCAGTCTTGGAGATCAAGCCTCCATCTCTTGCAGATCT
AGTCAGAGCATTGTACATAGTAATGGAAACACCTATTTAGAATGGTACTTGCAGAAACCAGGCCAGTCTCCAAAG
CTCCTGATCTACAAAGTTTTCAACCGATTTTCTGGGGTCCCAGACAGGTTCAGTGGCAGTGGATCAGGGACAGAT
TTCACACTCAAGATCAGCAGAGTGGAGGCTGAGGATCTGGGAGTTTATTACTGCTTTCAAGGTTCACATGTTCCG
CTCACGTTCGGTGCTGGGACCAAGCTGGAGCTGAAACGG

VLRendoMabB41
DVLMTQTPLSLPVSLGDQASISCRSSQSIVHSNGNTYLEWYLQKPGQSPKLLIYKVFNRFSGVPDRFS
GSGSGTDFTLKISRVEAEDLGVYYCFQGSHVPLTFGAGTKLELKR

FIG.6A

VHRendoMabB41
CAGGTCCAACTGCAGCAGCCTGGGGCTGAGCTTGTGAAGCCTGGGGCTTCAGTGAAGCTGTCCTGCAAGGCTTCT
GGCTACACCTTCACCAGCTACTGGATGCACTGGGTGAAGCAGAGGCCTGGACGAGGCCTTGAGTGGATTGGAAGG
ATTGATCCTGATAGTGGTGGTACTAAATACAATGAGAAGTTCAAGAGCAAGGCCACACTGACTGTAGACAAACCC
TCCAACACAGCCAACATGCAGCTCAGCAGCCTGACATCTGAAGACTCTGCGGTCTATTATTGTGTAAGAGAAGGG
TGGGACGCCTGGTTTGTTTACTGGGGCCAAGGGACTCTGCTCACTGTCTCTGCA

VHRendoMabB41
QVQLQQPGAELVKPGASVKLSCKASGYTFTSYWMHWVKQRPGRGLEWIGRIDPDSGGTKYNEKFKSKATLTVDKP
SNTANMQLSSLTSEDSAVYYCVREGWDAWFVYWGQGTLLTVSA

FIG.6B

VLRendoMabB36
GATGTTTTGATGACCCAAACTCCACTCTCCCTGCCTGTCAGTCTTGGAGATCAAGCCTCCATCTCTTGCAGATCT
AGTCAGAACATTGTCCATAGTAATGGATACACCTATTTAGAATGGTACCTGCAGAAACCAGGCCAGTCTCCAAAG
CTCCTGATCTACAAAGTTTCCAACCGATTTTCTGGGGTCCCAGACAGGTTCAGTGGCAGTGGATCAGGGACAGAT
TTCACACTCAAGATCAGCAGAGTGGAGGCTGAGGATCTGGGAGTTTATTACTGCTTTCAAGGTTCACATGTTCCT
CTCACGTTCGGCTCGGGGACAAAGTTGGAAATAAAACGG

VLRendoMabB36
DVLMTQTPLSLPVSLGDQASISCRSSQNIVHSNGYTYLEWYLQKPGQSPKLLIYKVSNRFSGVPDRFSGSGSGTD
FTLKISRVEAEDLGVYYCFQGSHVPLTFGSGTKLEIKR

FIG.7A

VHRendoMabB36
CAGGTCCAACTGCAGCAGCCTGGGGCTGAACTTGTGAAGCCTGGGGCTTCAGTGAAGCTGTCCTGCAAGGCTTCT
GGCTACACCTTCACCAGCTACTGGATACACTGGGTAAATCAGAGGCCTGGACGAGGCCTTGAGTGGATTGGAAGG
ATTGATCCTAATAGTGGTGGCACTAAGTACAATGAGAAGTTCAAGAGTAAGGCCACACTGACTGTAGACAAAACC
TCCAGCACAGCCTACATGCAGTTCAGCAGCCTGACATCTGAGGACTCTGCGGTCTATTATTGTGCAAGAGAGGGG
GAATTCGCCTGGTTTGCTTACTGGGGCCAAGGGACTCTGGTCACTGTCTCTGCA

VHRendoMabB36
QVQLQQPGAELVKPGASVKLSCKASGYTFTSYWIHWVNQRPGRGLEWIGRIDPNSGGTKYNEKFKSKATLTVDKT
SSTAYMQFSSLTSEDSAVYYCAREGEFAWFAYWGQGTLVTVSA

FIG.7B

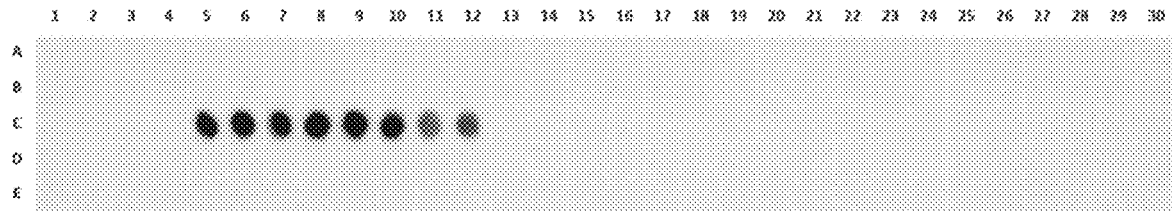

FIG.8A

Alignment of the peptides recognized by Rendomab-B49 with high intensity

```
      C5   SLAPAEVPKGDR
      C6    LAPAEVPKGDRT
      C7     APAEVPKGDRTA
      C8      PAEVPKGDRTAG
      C9       AEVPKGDRTAGS
     C10        EVPKGDRTAGSP
Consensus   ...paEVPKGDRtag..
```

FIG.8B

The sequence of the human endothelin receptor sub-type B

MQPPPSLCGRALVALVLACGLSRIWGEERGFPPDRATPLLQTAEIMTPPTKTLWPKGSNASLARSLAPAEVPKGD
RTAGSPPRTISPPPCQGPIEIKETFKYINTVVSCLVFVLGIIGNSTLLRIIYKNKCMRNGPNILIASLALGDLL
IVIDIPINVYKLLAEDWPFGAEMCKLVPFIQKASVGITVLSLCALSIDRYRAVASWSRIKGIGVPKWTAVEIVL
IWVVSVVLAVPEAIGFDIITMDYKGSYLRICLLHPVQKTAFMQFYKTAKDWWLFSFYFCLPLAITAFFYTLMTCEM
LRKKSGMQIALNDHLKQRREVAKTVFCLVLVFALCWLPLHLSRILKLTLYNQNDPNRCELLSFLLVLDYIGINMA
SLNSCINPIALYLVSKRFKNCFKSCLCCWCQSFEEKQSLEEKQSCLKFKANDHGYDNFRSSNKYSSS

MQPPPSLCGRALVALVLACGLSRIWG    Peptide signal
TRANSMEMBRANE REGIONS
EXTRACELLULAR REGIONS
INTRACELLULAR REGIONS
EVPKGDR                        Epitope recognized by Rendomab-B49

FIG.8C

SEQUENCE LISTING

```
<160> NUMBER OF SEQ ID NOS: 42

<210> SEQ ID NO 1
<211> LENGTH: 27
<212> TYPE: PRT
<213> ORGANISM: Unknown
<220> FEATURE:
<223> OTHER INFORMATION: Ordered juxtaposition of the CDRs of the heavy
      chain variable region

<400> SEQUENCE: 1

Gly Tyr Thr Phe Ile Ser Tyr Trp Ile Asp Pro Asp Ser Gly Gly Thr
1               5                   10                  15

Ala Arg Glu Gly Asp Tyr Ala Trp Phe Ala Tyr
            20                  25

<210> SEQ ID NO 2
<211> LENGTH: 23
<212> TYPE: PRT
<213> ORGANISM: Unknown
<220> FEATURE:
<223> OTHER INFORMATION: Ordered juxtaposition of the CDRs of the light
      chain variable region

<400> SEQUENCE: 2

Gln Ser Ile Val His Ser Asn Gly Asn Thr Tyr Lys Val Ser Phe Gln
1               5                   10                  15

Gly Ser His Val Pro Trp Thr
            20

<210> SEQ ID NO 3
<211> LENGTH: 8
<212> TYPE: PRT
<213> ORGANISM: unknown
<220> FEATURE:
<223> OTHER INFORMATION: Consensus sequence for CDR1H
<220> FEATURE:
<221> NAME/KEY: MISC_FEATURE
<222> LOCATION: (5)..(5)
<223> OTHER INFORMATION: X represents any amino acid and, in particular,
      either I, or T

<400> SEQUENCE: 3
```

Gly Tyr Thr Phe Xaa Ser Tyr Trp
1               5

<210> SEQ ID NO 4
<211> LENGTH: 24
<212> TYPE: DNA
<213> ORGANISM: Mus musculus
<220> FEATURE:
<221> NAME/KEY: CDS
<222> LOCATION: (1)..(24)
<223> OTHER INFORMATION: CDR1H of Rendomab B49

<400> SEQUENCE: 4 ggc tac acc ttc atc agc tac tgg                                    24
Gly Tyr Thr Phe Ile Ser Tyr Trp
1               5

<210> SEQ ID NO 5
<211> LENGTH: 8
<212> TYPE: PRT
<213> ORGANISM: Mus musculus

<400> SEQUENCE: 5

Gly Tyr Thr Phe Ile Ser Tyr Trp
1               5

<210> SEQ ID NO 6
<211> LENGTH: 24
<212> TYPE: DNA
<213> ORGANISM: Mus musculus
<220> FEATURE:
<221> NAME/KEY: CDS
<222> LOCATION: (1)..(24)
<223> OTHER INFORMATION: CDR1H of Rendomab B41 and Rendomab B36

<400> SEQUENCE: 6 ggc tac acc ttc acc agc tac tgg                                    24
Gly Tyr Thr Phe Thr Ser Tyr Trp
1               5

<210> SEQ ID NO 7
<211> LENGTH: 8
<212> TYPE: PRT
<213> ORGANISM: Mus musculus

<400> SEQUENCE: 7

Gly Tyr Thr Phe Thr Ser Tyr Trp
1               5

<210> SEQ ID NO 8
<211> LENGTH: 8
<212> TYPE: PRT
<213> ORGANISM: Unknown
<220> FEATURE:
<223> OTHER INFORMATION: Consensus sequence for CDR2H
<220> FEATURE:
<221> NAME/KEY: MISC_FEATURE
<222> LOCATION: (4)..(4)
<223> OTHER INFORMATION: X represents any amino acid and, in particular,
      either D, or N

<400> SEQUENCE: 8

Ile Asp Pro Xaa Ser Gly Gly Thr
1               5

<210> SEQ ID NO 9
<211> LENGTH: 24
<212> TYPE: DNA

```
<213> ORGANISM: Mus musculus
<220> FEATURE:
<221> NAME/KEY: misc_feature
<222> LOCATION: (1)..(24)
<223> OTHER INFORMATION: Sequence coding CDR2H of Rendomab B49 (N = C)
      or of Rendomab B41 (N = T)
<220> FEATURE:
<221> NAME/KEY: misc_feature
<222> LOCATION: (15)..(15)
<223> OTHER INFORMATION: N represents either C, or T

<400> SEQUENCE: 9
attgatcctg atagnggtgg tact                                          24

<210> SEQ ID NO 10
<211> LENGTH: 8
<212> TYPE: PRT
<213> ORGANISM: Mus musculus
<220> FEATURE:
<221> NAME/KEY: DOMAIN
<222> LOCATION: (1)..(8)
<223> OTHER INFORMATION: CDR2H of Rendomab B49 and of Rendomab B41

<400> SEQUENCE: 10

Ile Asp Pro Asp Ser Gly Gly Thr
1               5

<210> SEQ ID NO 11
<211> LENGTH: 24
<212> TYPE: DNA
<213> ORGANISM: Mus musculus
<220> FEATURE:
<221> NAME/KEY: CDS
<222> LOCATION: (1)..(24)
<223> OTHER INFORMATION: CDR2H of Rendomab B36

<400> SEQUENCE: 11 att gat cct aat agt ggt ggc act                                     24
Ile Asp Pro Asn Ser Gly Gly Thr
1               5

<210> SEQ ID NO 12
<211> LENGTH: 8
<212> TYPE: PRT
<213> ORGANISM: Mus musculus

<400> SEQUENCE: 12

Ile Asp Pro Asn Ser Gly Gly Thr
1               5

<210> SEQ ID NO 13
<211> LENGTH: 11
<212> TYPE: PRT
<213> ORGANISM: Unknown
<220> FEATURE:
<223> OTHER INFORMATION: Consensus sequence for CDR3H
<220> FEATURE:
<221> NAME/KEY: MISC_FEATURE
<222> LOCATION: (1)..(1)
<223> OTHER INFORMATION: X represents any amino acid and, in particular,
      is selected from A, D, Y, E, F, V and W and, more particularly, it
      is either A, or V
<220> FEATURE:
<221> NAME/KEY: MISC_FEATURE
<222> LOCATION: (5)..(5)
<223> OTHER INFORMATION: X represents any amino acid and, in particular,
      is selected from A, D, Y, E, F, V and W and, more particularly, is
      selected from D, W and E
<220> FEATURE:
<221> NAME/KEY: MISC_FEATURE
<222> LOCATION: (6)..(6)
```

-continued

```
<223> OTHER INFORMATION: X represents any amino acid and, in particular,
      is selected from A, D, Y, E, F, V and W and, more particularly, is
      selected from Y, D and F
<220> FEATURE:
<221> NAME/KEY: MISC_FEATURE
<222> LOCATION: (10)..(10)
<223> OTHER INFORMATION: X represents any amino acid and, in particular,
      is selected from A, D, Y, E, F, V and W and, more particularly, is
      either A, or V

<400> SEQUENCE: 13

Xaa Arg Glu Gly Xaa Xaa Ala Trp Phe Xaa Tyr
1               5                   10

<210> SEQ ID NO 14
<211> LENGTH: 33
<212> TYPE: DNA
<213> ORGANISM: Mus musculus
<220> FEATURE:
<221> NAME/KEY: CDS
<222> LOCATION: (1)..(33)
<223> OTHER INFORMATION: CDR3H of Rendomab B49

<400> SEQUENCE: 14 gca aga gaa ggg gat tac gcc tgg ttt gct tac                    33
Ala Arg Glu Gly Asp Tyr Ala Trp Phe Ala Tyr
1               5                   10

<210> SEQ ID NO 15
<211> LENGTH: 11
<212> TYPE: PRT
<213> ORGANISM: Mus musculus

<400> SEQUENCE: 15

Ala Arg Glu Gly Asp Tyr Ala Trp Phe Ala Tyr
1               5                   10

<210> SEQ ID NO 16
<211> LENGTH: 33
<212> TYPE: DNA
<213> ORGANISM: Mus musculus
<220> FEATURE:
<221> NAME/KEY: CDS
<222> LOCATION: (1)..(33)
<223> OTHER INFORMATION: CDR3H of Rendomab B41

<400> SEQUENCE: 16 gta aga gaa ggg tgg gac gcc tgg ttt gtt tac                    33
Val Arg Glu Gly Trp Asp Ala Trp Phe Val Tyr
1               5                   10

<210> SEQ ID NO 17
<211> LENGTH: 11
<212> TYPE: PRT
<213> ORGANISM: Mus musculus

<400> SEQUENCE: 17

Val Arg Glu Gly Trp Asp Ala Trp Phe Val Tyr
1               5                   10

<210> SEQ ID NO 18
<211> LENGTH: 33
<212> TYPE: DNA
<213> ORGANISM: Mus musculus
<220> FEATURE:
<221> NAME/KEY: CDS
<222> LOCATION: (1)..(33)
<223> OTHER INFORMATION: CDR3H of Rendomab B36
```

<400> SEQUENCE: 18

```
gca aga gag ggg gaa ttc gcc tgg ttt gct tac                          33
Ala Arg Glu Gly Glu Phe Ala Trp Phe Ala Tyr
1               5                   10
```

<210> SEQ ID NO 19
<211> LENGTH: 11
<212> TYPE: PRT
<213> ORGANISM: Mus musculus

<400> SEQUENCE: 19

```
Ala Arg Glu Gly Glu Phe Ala Trp Phe Ala Tyr
1               5                   10
```

<210> SEQ ID NO 20
<211> LENGTH: 11
<212> TYPE: PRT
<213> ORGANISM: Unknown
<220> FEATURE:
<223> OTHER INFORMATION: Consensus sequence for CDR1L
<220> FEATURE:
<221> NAME/KEY: MISC_FEATURE
<222> LOCATION: (2)..(2)
<223> OTHER INFORMATION: X represents any amino acid and, in particular,
      is selected from N, Y and S and, more particularly, is either N,
      or S
<220> FEATURE:
<221> NAME/KEY: MISC_FEATURE
<222> LOCATION: (9)..(9)
<223> OTHER INFORMATION: X represents any amino acid and, in particular,
      is selected from N, Y and S and, more particularly, is either N,
      or Y

<400> SEQUENCE: 20

```
Gln Xaa Ile Val His Ser Asn Gly Xaa Thr Tyr
1               5                   10
```

<210> SEQ ID NO 21
<211> LENGTH: 33
<212> TYPE: DNA
<213> ORGANISM: Mus musculus
<220> FEATURE:
<221> NAME/KEY: CDS
<222> LOCATION: (1)..(33)
<223> OTHER INFORMATION: CDR1L of Rendomab B49 and of Rendomab B41

<400> SEQUENCE: 21

```
cag agc att gta cat agt aat gga aac acc tat                          33
Gln Ser Ile Val His Ser Asn Gly Asn Thr Tyr
1               5                   10
```

<210> SEQ ID NO 22
<211> LENGTH: 11
<212> TYPE: PRT
<213> ORGANISM: Mus musculus

<400> SEQUENCE: 22

```
Gln Ser Ile Val His Ser Asn Gly Asn Thr Tyr
1               5                   10
```

<210> SEQ ID NO 23
<211> LENGTH: 33
<212> TYPE: DNA
<213> ORGANISM: Mus musculus
<220> FEATURE:
<221> NAME/KEY: CDS
<222> LOCATION: (1)..(33)
<223> OTHER INFORMATION: CDR1L of Rendomab B36

```
<400> SEQUENCE: 23 cag aac att gtc cat agt aat gga tac acc tat                           33
Gln Asn Ile Val His Ser Asn Gly Tyr Thr Tyr
1               5                   10

<210> SEQ ID NO 24
<211> LENGTH: 11
<212> TYPE: PRT
<213> ORGANISM: Mus musculus

<400> SEQUENCE: 24

Gln Asn Ile Val His Ser Asn Gly Tyr Thr Tyr
1               5                   10

<210> SEQ ID NO 25
<211> LENGTH: 9
<212> TYPE: PRT
<213> ORGANISM: Unknown
<220> FEATURE:
<223> OTHER INFORMATION: Consensus sequence for CDR3L
<220> FEATURE:
<221> NAME/KEY: MISC_FEATURE
<222> LOCATION: (8)..(8)
<223> OTHER INFORMATION: X represents any amino acid and, in particular,
      is either W, or L

<400> SEQUENCE: 25

Phe Gln Gly Ser His Val Pro Xaa Thr
1               5

<210> SEQ ID NO 26
<211> LENGTH: 27
<212> TYPE: DNA
<213> ORGANISM: Mus musculus
<220> FEATURE:
<221> NAME/KEY: CDS
<222> LOCATION: (1)..(27)
<223> OTHER INFORMATION: CDR3L of Rendomab B49

<400> SEQUENCE: 26 ttt caa ggt tca cat gtt ccg tgg acg                                   27
Phe Gln Gly Ser His Val Pro Trp Thr
1               5

<210> SEQ ID NO 27
<211> LENGTH: 9
<212> TYPE: PRT
<213> ORGANISM: Mus musculus

<400> SEQUENCE: 27

Phe Gln Gly Ser His Val Pro Trp Thr
1               5

<210> SEQ ID NO 28
<211> LENGTH: 27
<212> TYPE: DNA
<213> ORGANISM: Mus musculus
<220> FEATURE:
<221> NAME/KEY: misc_feature
<222> LOCATION: (1)..(27)
<223> OTHER INFORMATION: Sequence coding CDR3L of Rendomab B41 and of
      Rendomab B36
<220> FEATURE:
<221> NAME/KEY: misc_feature
<222> LOCATION: (21)..(21)
<223> OTHER INFORMATION: N represents either G, or T

<400> SEQUENCE: 28
```

```
tttcaaggtt cacatgttcc nctcacg                                            27
```

<210> SEQ ID NO 29
<211> LENGTH: 9
<212> TYPE: PRT
<213> ORGANISM: Mus musculus
<220> FEATURE:
<221> NAME/KEY: DOMAIN
<222> LOCATION: (1)..(9)
<223> OTHER INFORMATION: CDR3L of Rendomab B41 and of Rendomab B36

<400> SEQUENCE: 29

Phe Gln Gly Ser His Val Pro Leu Thr
1               5

<210> SEQ ID NO 30
<211> LENGTH: 354
<212> TYPE: DNA
<213> ORGANISM: Mus musculus
<220> FEATURE:
<221> NAME/KEY: CDS
<222> LOCATION: (1)..(354)
<223> OTHER INFORMATION: Heavy chain variable region of Rendomab B49

<400> SEQUENCE: 30

```
cag gtc caa ctg cag cag cct ggg gct gcg ctt gtg aag cct ggg gct      48
Gln Val Gln Leu Gln Gln Pro Gly Ala Ala Leu Val Lys Pro Gly Ala
1               5                   10                  15 tca gtg aag ctg tcc tgc aag gct tct ggc tac acc ttc atc agc tac      96
Ser Val Lys Leu Ser Cys Lys Ala Ser Gly Tyr Thr Phe Ile Ser Tyr
            20                  25                  30 tgg atg ctc tgg gtg aag cag agg cct gga cga ggc ctt gag tgg att     144
Trp Met Leu Trp Val Lys Gln Arg Pro Gly Arg Gly Leu Glu Trp Ile
        35                  40                  45 gga agg att gat cct gat agc ggt ggt act aag tac aat gag aag ttc     192
Gly Arg Ile Asp Pro Asp Ser Gly Gly Thr Lys Tyr Asn Glu Lys Phe
    50                  55                  60 aag agc aag gcc aca ctg act gta gac aaa tcc tcc agc aca gcc tac     240
Lys Ser Lys Ala Thr Leu Thr Val Asp Lys Ser Ser Ser Thr Ala Tyr
65                  70                  75                  80 atg cag ctc agc agc ctg aca tct gag gac tct gcg gtc tat tat tgt     288
Met Gln Leu Ser Ser Leu Thr Ser Glu Asp Ser Ala Val Tyr Tyr Cys
                85                  90                  95 gca aga gaa ggg gat tac gcc tgg ttt gct tac tgg ggc caa ggg act     336
Ala Arg Glu Gly Asp Tyr Ala Trp Phe Ala Tyr Trp Gly Gln Gly Thr
            100                 105                 110 ctg gtc cct gtc tct gca                                              354
Leu Val Pro Val Ser Ala
        115
```

<210> SEQ ID NO 31
<211> LENGTH: 118
<212> TYPE: PRT
<213> ORGANISM: Mus musculus

<400> SEQUENCE: 31

Gln Val Gln Leu Gln Gln Pro Gly Ala Ala Leu Val Lys Pro Gly Ala
1               5                   10                  15

Ser Val Lys Leu Ser Cys Lys Ala Ser Gly Tyr Thr Phe Ile Ser Tyr
            20                  25                  30

Trp Met Leu Trp Val Lys Gln Arg Pro Gly Arg Gly Leu Glu Trp Ile
        35                  40                  45

Gly Arg Ile Asp Pro Asp Ser Gly Gly Thr Lys Tyr Asn Glu Lys Phe

```
                50                  55                  60
Lys Ser Lys Ala Thr Leu Thr Val Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Glu Gly Asp Tyr Ala Trp Phe Ala Tyr Trp Gly Gln Gly Thr
                100                 105                 110

Leu Val Pro Val Ser Ala
        115

<210> SEQ ID NO 32
<211> LENGTH: 354
<212> TYPE: DNA
<213> ORGANISM: Mus musculus
<220> FEATURE:
<221> NAME/KEY: CDS
<222> LOCATION: (1)..(354)
<223> OTHER INFORMATION: Heavy chain variable region of Rendomab B41

<400> SEQUENCE: 32 cag gtc caa ctg cag cag cct ggg gct gag ctt gtg aag cct ggg gct       48
Gln Val Gln Leu Gln Gln Pro Gly Ala Glu Leu Val Lys Pro Gly Ala
 1               5                  10                  15 tca gtg aag ctg tcc tgc aag gct tct ggc tac acc ttc acc agc tac       96
Ser Val Lys Leu Ser Cys Lys Ala Ser Gly Tyr Thr Phe Thr Ser Tyr
                 20                  25                  30 tgg atg cac tgg gtg aag cag agg cct gga cga ggc ctt gag tgg att      144
Trp Met His Trp Val Lys Gln Arg Pro Gly Arg Gly Leu Glu Trp Ile
             35                  40                  45 gga agg att gat cct gat agt ggt ggt act aaa tac aat gag aag ttc      192
Gly Arg Ile Asp Pro Asp Ser Gly Gly Thr Lys Tyr Asn Glu Lys Phe
         50                  55                  60 aag agc aag gcc aca ctg act gta gac aaa ccc tcc aac aca gcc aac      240
Lys Ser Lys Ala Thr Leu Thr Val Asp Lys Pro Ser Asn Thr Ala Asn
 65                  70                  75                  80 atg cag ctc agc agc ctg aca tct gaa gac tct gcg gtc tat tat tgt      288
Met Gln Leu Ser Ser Leu Thr Ser Glu Asp Ser Ala Val Tyr Tyr Cys
                 85                  90                  95 gta aga gaa ggg tgg gac gcc tgg ttt gtt tac tgg ggc caa ggg act      336
Val Arg Glu Gly Trp Asp Ala Trp Phe Val Tyr Trp Gly Gln Gly Thr
                100                 105                 110 ctg ctc act gtc tct gca                                              354
Leu Leu Thr Val Ser Ala
        115

<210> SEQ ID NO 33
<211> LENGTH: 118
<212> TYPE: PRT
<213> ORGANISM: Mus musculus

<400> SEQUENCE: 33

Gln Val Gln Leu Gln Gln Pro Gly Ala Glu Leu Val Lys Pro Gly Ala
 1               5                  10                  15

Ser Val Lys Leu Ser Cys Lys Ala Ser Gly Tyr Thr Phe Thr Ser Tyr
                 20                  25                  30

Trp Met His Trp Val Lys Gln Arg Pro Gly Arg Gly Leu Glu Trp Ile
             35                  40                  45

Gly Arg Ile Asp Pro Asp Ser Gly Gly Thr Lys Tyr Asn Glu Lys Phe
         50                  55                  60

Lys Ser Lys Ala Thr Leu Thr Val Asp Lys Pro Ser Asn Thr Ala Asn
```

```
                    65                  70                  75                  80
Met Gln Leu Ser Ser Leu Thr Ser Glu Asp Ser Ala Val Tyr Tyr Cys
                        85                  90                  95

Val Arg Glu Gly Trp Asp Ala Trp Phe Val Tyr Trp Gly Gln Gly Thr
                100                 105                 110

Leu Leu Thr Val Ser Ala
        115

<210> SEQ ID NO 34
<211> LENGTH: 354
<212> TYPE: DNA
<213> ORGANISM: Mus musculus
<220> FEATURE:
<221> NAME/KEY: CDS
<222> LOCATION: (1)..(354)
<223> OTHER INFORMATION: Heavy chain variable region of Rendomab B36

<400> SEQUENCE: 34 cag gtc caa ctg cag cag cct ggg gct gaa ctt gtg aag cct ggg gct      48
Gln Val Gln Leu Gln Gln Pro Gly Ala Glu Leu Val Lys Pro Gly Ala
1               5                   10                  15 tca gtg aag ctg tcc tgc aag gct tct ggc tac acc ttc acc agc tac      96
Ser Val Lys Leu Ser Cys Lys Ala Ser Gly Tyr Thr Phe Thr Ser Tyr
            20                  25                  30 tgg ata cac tgg gta aat cag agg cct gga cga ggc ctt gag tgg att     144
Trp Ile His Trp Val Asn Gln Arg Pro Gly Arg Gly Leu Glu Trp Ile
        35                  40                  45 gga agg att gat cct aat agt ggt ggc act aag tac aat gag aag ttc     192
Gly Arg Ile Asp Pro Asn Ser Gly Gly Thr Lys Tyr Asn Glu Lys Phe
    50                  55                  60 aag agt aag gcc aca ctg act gta gac aaa acc tcc agc aca gcc tac     240
Lys Ser Lys Ala Thr Leu Thr Val Asp Lys Thr Ser Ser Thr Ala Tyr
65                  70                  75                  80 atg cag ttc agc agc ctg aca tct gag gac tct gcg gtc tat tat tgt     288
Met Gln Phe Ser Ser Leu Thr Ser Glu Asp Ser Ala Val Tyr Tyr Cys
                85                  90                  95 gca aga gag ggg gaa ttc gcc tgg ttt gct tac tgg ggc caa ggg act     336
Ala Arg Glu Gly Glu Phe Ala Trp Phe Ala Tyr Trp Gly Gln Gly Thr
            100                 105                 110 ctg gtc act gtc tct gca                                             354
Leu Val Thr Val Ser Ala
        115

<210> SEQ ID NO 35
<211> LENGTH: 118
<212> TYPE: PRT
<213> ORGANISM: Mus musculus

<400> SEQUENCE: 35

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Ile His Trp Val Asn Gln Arg Pro Gly Arg Gly Leu Glu Trp Ile
        35                  40                  45

Gly Arg Ile Asp Pro Asn Ser Gly Gly Thr Lys Tyr Asn Glu Lys Phe
    50                  55                  60

Lys Ser Lys Ala Thr Leu Thr Val Asp Lys Thr Ser Ser Thr Ala Tyr
65                  70                  75                  80

Met Gln Phe Ser Ser Leu Thr Ser Glu Asp Ser Ala Val Tyr Tyr Cys
```

```
                    85                  90                  95
Ala Arg Glu Gly Glu Phe Ala Trp Phe Ala Tyr Trp Gly Gln Gly Thr
                100                 105                 110

Leu Val Thr Val Ser Ala
        115

<210> SEQ ID NO 36
<211> LENGTH: 336
<212> TYPE: DNA
<213> ORGANISM: Mus musculus
<220> FEATURE:
<221> NAME/KEY: CDS
<222> LOCATION: (1)..(336)
<223> OTHER INFORMATION: Light chain variable region of Rendomab B49

<400> SEQUENCE: 36 gat gtt ttg atg acc caa act cca ctc tcc ctg cct gtc agt ctt gga       48
Asp Val Leu Met Thr Gln Thr Pro Leu Ser Leu Pro Val Ser Leu Gly
1               5                   10                  15 gat caa gcc tcc atc tct tgc aga tct agt cag agc att gta cat agt       96
Asp Gln Ala Ser Ile Ser Cys Arg Ser Ser Gln Ser Ile Val His Ser
                20                  25                  30 aat gga aac acc tat tta gaa tgg tac ctg cag aaa cca ggc cag tct      144
Asn Gly Asn Thr Tyr Leu Glu Trp Tyr Leu Gln Lys Pro Gly Gln Ser
            35                  40                  45 cca aag ctc ctg atc tac aaa gtt tcc aac cga ttt tct ggg gtc cca      192
Pro Lys Leu Leu Ile Tyr Lys Val Ser Asn Arg Phe Ser Gly Val Pro
        50                  55                  60 gac agg ttc agt ggc agt gga tca ggg aca gat ttc aca ctc aag atc      240
Asp Arg Phe Ser Gly Ser Gly Ser Gly Thr Asp Phe Thr Leu Lys Ile
65                  70                  75                  80 agc aga gtg gag gct gag gat ctg gga gtt tat tac tgc ttt caa ggt      288
Ser Arg Val Glu Ala Glu Asp Leu Gly Val Tyr Tyr Cys Phe Gln Gly
                85                  90                  95 tca cat gtt ccg tgg acg ttc ggt gga ggc acc aag ctg gaa atc aaa      336
Ser His Val Pro Trp Thr Phe Gly Gly Gly Thr Lys Leu Glu Ile Lys
                100                 105                 110

<210> SEQ ID NO 37
<211> LENGTH: 112
<212> TYPE: PRT
<213> ORGANISM: Mus musculus

<400> SEQUENCE: 37

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
                100                 105                 110

<210> SEQ ID NO 38
```

```
<211> LENGTH: 339
<212> TYPE: DNA
<213> ORGANISM: Mus musculus
<220> FEATURE:
<221> NAME/KEY: CDS
<222> LOCATION: (1)..(339)
<223> OTHER INFORMATION: Light chain variable region of Rendomab B41

<400> SEQUENCE: 38 gat gtt ttg atg acc caa act cca ctc tcc ctg cct gtc agt ctt gga      48
Asp Val Leu Met Thr Gln Thr Pro Leu Ser Leu Pro Val Ser Leu Gly
1               5                   10                  15 gat caa gcc tcc atc tct tgc aga tct agt cag agc att gta cat agt      96
Asp Gln Ala Ser Ile Ser Cys Arg Ser Ser Gln Ser Ile Val His Ser
            20                  25                  30 aat gga aac acc tat tta gaa tgg tac ttg cag aaa cca ggc cag tct     144
Asn Gly Asn Thr Tyr Leu Glu Trp Tyr Leu Gln Lys Pro Gly Gln Ser
        35                  40                  45 cca aag ctc ctg atc tac aaa gtt ttc aac cga ttt tct ggg gtc cca     192
Pro Lys Leu Leu Ile Tyr Lys Val Phe Asn Arg Phe Ser Gly Val Pro
    50                  55                  60 gac agg ttc agt ggc agt gga tca ggg aca gat ttc aca ctc aag atc     240
Asp Arg Phe Ser Gly Ser Gly Ser Gly Thr Asp Phe Thr Leu Lys Ile
65                  70                  75                  80 agc aga gtg gag gct gag gat ctg gga gtt tat tac tgc ttt caa ggt     288
Ser Arg Val Glu Ala Glu Asp Leu Gly Val Tyr Tyr Cys Phe Gln Gly
                85                  90                  95 tca cat gtt ccg ctc acg ttc ggt gct ggg acc aag ctg gag ctg aaa     336
Ser His Val Pro Leu Thr Phe Gly Ala Gly Thr Lys Leu Glu Leu Lys
                100                 105                 110 cgg                                                                  339
Arg

<210> SEQ ID NO 39
<211> LENGTH: 113
<212> TYPE: PRT
<213> ORGANISM: Mus musculus

<400> SEQUENCE: 39

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Phe Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
                100                 105                 110

Arg

<210> SEQ ID NO 40
<211> LENGTH: 339
<212> TYPE: DNA
<213> ORGANISM: Mus musculus
<220> FEATURE:
<221> NAME/KEY: CDS
```

```
<222> LOCATION: (1)..(339)
<223> OTHER INFORMATION: Light chain variable region of Rendomab B36

<400> SEQUENCE: 40 gat gtt ttg atg acc caa act cca ctc tcc ctg cct gtc agt ctt gga       48
Asp Val Leu Met Thr Gln Thr Pro Leu Ser Leu Pro Val Ser Leu Gly
1               5                   10                  15 gat caa gcc tcc atc tct tgc aga tct agt cag aac att gtc cat agt       96
Asp Gln Ala Ser Ile Ser Cys Arg Ser Ser Gln Asn Ile Val His Ser
            20                  25                  30 aat gga tac acc tat tta gaa tgg tac ctg cag aaa cca ggc cag tct      144
Asn Gly Tyr Thr Tyr Leu Glu Trp Tyr Leu Gln Lys Pro Gly Gln Ser
        35                  40                  45 cca aag ctc ctg atc tac aaa gtt tcc aac cga ttt tct ggg gtc cca      192
Pro Lys Leu Leu Ile Tyr Lys Val Ser Asn Arg Phe Ser Gly Val Pro
    50                  55                  60 gac agg ttc agt ggc agt gga tca ggg aca gat ttc aca ctc aag atc      240
Asp Arg Phe Ser Gly Ser Gly Ser Gly Thr Asp Phe Thr Leu Lys Ile
65                  70                  75                  80 agc aga gtg gag gct gag gat ctg gga gtt tat tac tgc ttt caa ggt      288
Ser Arg Val Glu Ala Glu Asp Leu Gly Val Tyr Tyr Cys Phe Gln Gly
                85                  90                  95 tca cat gtt cct ctc acg ttc ggc tcg ggg aca aag ttg gaa ata aaa      336
Ser His Val Pro Leu Thr Phe Gly Ser Gly Thr Lys Leu Glu Ile Lys
            100                 105                 110 cgg                                                                  339
Arg

<210> SEQ ID NO 41
<211> LENGTH: 113
<212> TYPE: PRT
<213> ORGANISM: Mus musculus

<400> SEQUENCE: 41

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Asn Gly Tyr Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ser Gly Thr Lys Leu Glu Ile Lys
            100                 105                 110

Arg

<210> SEQ ID NO 42
<211> LENGTH: 442
<212> TYPE: PRT
<213> ORGANISM: Homo sapiens
<220> FEATURE:
<221> NAME/KEY: CHAIN
<222> LOCATION: (1)..(442)
<223> OTHER INFORMATION: Sequence of the human endothelin receptor
      sub-type B
<220> FEATURE:
<221> NAME/KEY: CHAIN
```

```
<222> LOCATION: (1)..(101)
<223> OTHER INFORMATION: Extracellular region
<220> FEATURE:
<221> NAME/KEY: SIGNAL
<222> LOCATION: (1)..(26)
<223> OTHER INFORMATION: Signal peptide
<220> FEATURE:
<221> NAME/KEY: MISC_FEATURE
<222> LOCATION: (64)..(64)
<223> OTHER INFORMATION: Proteolysis site
<220> FEATURE:
<221> NAME/KEY: CHAIN
<222> LOCATION: (65)..(76)
<223> OTHER INFORMATION: Peptide C5
<220> FEATURE:
<221> NAME/KEY: CHAIN
<222> LOCATION: (66)..(77)
<223> OTHER INFORMATION: Peptide C6
<220> FEATURE:
<221> NAME/KEY: CHAIN
<222> LOCATION: (67)..(78)
<223> OTHER INFORMATION: Peptide C7
<220> FEATURE:
<221> NAME/KEY: CHAIN
<222> LOCATION: (68)..(79)
<223> OTHER INFORMATION: Peptide C8
<220> FEATURE:
<221> NAME/KEY: CHAIN
<222> LOCATION: (69)..(80)
<223> OTHER INFORMATION: Peptide C9
<220> FEATURE:
<221> NAME/KEY: CHAIN
<222> LOCATION: (70)..(81)
<223> OTHER INFORMATION: Peptide C10
<220> FEATURE:
<221> NAME/KEY: CHAIN
<222> LOCATION: (70)..(76)
<223> OTHER INFORMATION: Epitope recognized by Rendomab-B49
<220> FEATURE:
<221> NAME/KEY: CHAIN
<222> LOCATION: (71)..(82)
<223> OTHER INFORMATION: Peptide C11
<220> FEATURE:
<221> NAME/KEY: CHAIN
<222> LOCATION: (72)..(83)
<223> OTHER INFORMATION: Peptide C12
<220> FEATURE:
<221> NAME/KEY: CHAIN
<222> LOCATION: (102)..(126)
<223> OTHER INFORMATION: Transmembrane region
<220> FEATURE:
<221> NAME/KEY: CHAIN
<222> LOCATION: (127)..(137)
<223> OTHER INFORMATION: Intracellular region
<220> FEATURE:
<221> NAME/KEY: CHAIN
<222> LOCATION: (138)..(163)
<223> OTHER INFORMATION: Transmembrane region
<220> FEATURE:
<221> NAME/KEY: CHAIN
<222> LOCATION: (164)..(175)
<223> OTHER INFORMATION: Extracellular region
<220> FEATURE:
<221> NAME/KEY: CHAIN
<222> LOCATION: (176)..(197)
<223> OTHER INFORMATION: Transmembrane region
<220> FEATURE:
<221> NAME/KEY: CHAIN
<222> LOCATION: (198)..(218)
<223> OTHER INFORMATION: Intracellular region
<220> FEATURE:
<221> NAME/KEY: CHAIN
<222> LOCATION: (219)..(243)
<223> OTHER INFORMATION: Transmembrane region
<220> FEATURE:
<221> NAME/KEY: CHAIN
<222> LOCATION: (244)..(274)
<223> OTHER INFORMATION: Extracellular region
<220> FEATURE:
```

<221> NAME/KEY: CHAIN
<222> LOCATION: (275)..(296)
<223> OTHER INFORMATION: Transmembrane region
<220> FEATURE:
<221> NAME/KEY: CHAIN
<222> LOCATION: (297)..(324)
<223> OTHER INFORMATION: Intracellular region
<220> FEATURE:
<221> NAME/KEY: CHAIN
<222> LOCATION: (325)..(350)
<223> OTHER INFORMATION: Transmembrane region
<220> FEATURE:
<221> NAME/KEY: CHAIN
<222> LOCATION: (351)..(362)
<223> OTHER INFORMATION: Extracellular region
<220> FEATURE:
<221> NAME/KEY: CHAIN
<222> LOCATION: (363)..(389)
<223> OTHER INFORMATION: Transmembrane region
<220> FEATURE:
<221> NAME/KEY: CHAIN
<222> LOCATION: (390)..(442)
<223> OTHER INFORMATION: Intracellular region

<400> SEQUENCE: 42

```
Met Gln Pro Pro Ser Leu Cys Gly Arg Ala Leu Val Ala Leu Val
1               5                   10                  15

Leu Ala Cys Gly Leu Ser Arg Ile Trp Gly Glu Glu Arg Gly Phe Pro
            20                  25                  30

Pro Asp Arg Ala Thr Pro Leu Leu Gln Thr Ala Glu Ile Met Thr Pro
        35                  40                  45

Pro Thr Lys Thr Leu Trp Pro Lys Gly Ser Asn Ala Ser Leu Ala Arg
    50                  55                  60

Ser Leu Ala Pro Ala Glu Val Pro Lys Gly Asp Arg Thr Ala Gly Ser
65              70                  75                  80

Pro Pro Arg Thr Ile Ser Pro Pro Cys Gln Gly Pro Ile Glu Ile
            85                  90                  95

Lys Glu Thr Phe Lys Tyr Ile Asn Thr Val Val Ser Cys Leu Val Phe
            100                 105                 110

Val Leu Gly Ile Ile Gly Asn Ser Thr Leu Leu Arg Ile Ile Tyr Lys
        115                 120                 125

Asn Lys Cys Met Arg Asn Gly Pro Asn Ile Leu Ile Ala Ser Leu Ala
    130                 135                 140

Leu Gly Asp Leu Leu His Ile Val Ile Asp Ile Pro Ile Asn Val Tyr
145             150                 155                 160

Lys Leu Leu Ala Glu Asp Trp Pro Phe Gly Ala Glu Met Cys Lys Leu
            165                 170                 175

Val Pro Phe Ile Gln Lys Ala Ser Val Gly Ile Thr Val Leu Ser Leu
        180                 185                 190

Cys Ala Leu Ser Ile Asp Arg Tyr Arg Ala Val Ala Ser Trp Ser Arg
    195                 200                 205

Ile Lys Gly Ile Gly Val Pro Lys Trp Thr Ala Val Glu Ile Val Leu
210                 215                 220

Ile Trp Val Val Ser Val Val Leu Ala Val Pro Glu Ala Ile Gly Phe
225                 230                 235                 240

Asp Ile Ile Thr Met Asp Tyr Lys Gly Ser Tyr Leu Arg Ile Cys Leu
            245                 250                 255

Leu His Pro Val Gln Lys Thr Ala Phe Met Gln Phe Tyr Lys Thr Ala
        260                 265                 270

Lys Asp Trp Trp Leu Phe Ser Phe Tyr Phe Cys Leu Pro Leu Ala Ile
    275                 280                 285
```

```
Thr Ala Phe Phe Tyr Thr Leu Met Thr Cys Glu Met Leu Arg Lys Lys
    290                 295                 300

Ser Gly Met Gln Ile Ala Leu Asn Asp His Leu Lys Gln Arg Arg Glu
305                 310                 315                 320

Val Ala Lys Thr Val Phe Cys Leu Val Leu Val Phe Ala Leu Cys Trp
                325                 330                 335

Leu Pro Leu His Leu Ser Arg Ile Leu Lys Leu Thr Leu Tyr Asn Gln
                340                 345                 350

Asn Asp Pro Asn Arg Cys Glu Leu Leu Ser Phe Leu Leu Val Leu Asp
            355                 360                 365

Tyr Ile Gly Ile Asn Met Ala Ser Leu Asn Ser Cys Ile Asn Pro Ile
    370                 375                 380

Ala Leu Tyr Leu Val Ser Lys Arg Phe Lys Asn Cys Phe Lys Ser Cys
385                 390                 395                 400

Leu Cys Cys Trp Cys Gln Ser Phe Glu Glu Lys Gln Ser Leu Glu Glu
                405                 410                 415

Lys Gln Ser Cys Leu Lys Phe Lys Ala Asn Asp His Gly Tyr Asp Asn
                420                 425                 430

Phe Arg Ser Ser Asn Lys Tyr Ser Ser Ser
            435                 440
```

ANTIBODY DIRECTED AGAINST THE ENDOTHELIN RECEPTOR BETA SUB-TYPE

CROSS-REFERENCE TO RELATED APPLICATIONS

This is a National Stage application of PCT international application PCT/EP2017/065442, filed on Jun. 22, 2017, which claims the priority of French Patent Application No. 16 55915, filed Jun. 24, 2016, both of which are incorporated herein by reference in their entirety.

TECHNICAL FIELD

The present invention relates to the technical field of antibodies, their therapeutic and diagnostic use as well as their use as a research tool.

More particularly, the present invention provides antibodies, advantageously monoclonal antibodies, specific to the native and functional conformation of the endothelin receptor sub-type B and in particular human endothelin receptors expressed at the surface of cancer cells such as glioblastoma cells.

The present invention relates to the use of these antibodies for therapeutic and diagnostic purposes as well as research purposes.

State of Prior Art

Receptors of different endothelins (designated ET1, ET2 and ET3 in humans) belong to the family of receptors with 7 transmembrane domains also called GPCRs for "G Protein Coupled Receptors". Endothelin receptors have, in humans, two main sub-types which are sub-type A (ETA-R) and sub-type B (ETB-R). The fact that these receptors are classified in the GPCR family provides them with a complex three-dimensional structure. This feature partly explains the difficulty to obtain antibodies recognising the native structure of these receptors which is expressed to the cellular membrane. In fact, the difficulty to obtain monoclonal antibodies specific to the GPCRs is a consequence of problems related to obtaining these receptors, in a native and functional form, outside their membrane context.

The endothelin axis and its receptors are implied in several physiopathological functions and dysfunctions. By way of non-limiting examples, arterial hypertension, atherosclerosis, coronary artery diseases, liver dysfunctions, cerebrovascular diseases, Crohn's disease, pulmonary fibrosis, asthma, etc. can be mentioned (see for review R. Shah, 2007, "Endothelins in health and disease", Eur. J. Int. Med., vol. 18, pages 272-282).

Moreover, endothelin receptors also turned out to be associated with the development of many cancers, by promoting proliferation, survival and dissemination of cancer cells as well as angiogenesis (Bagnato & Rosano, 2008, "The endothelin axis in cancer", Int. J. of Biochem. & Cell Biology, vol. 40, pages 1443-1451). As regards the endothelin receptor sub-type B, the latter has a modification of its expression level in particular in melanomas, colon cancer, Kaposi's sarcoma, glioblastomas (brain tumors), and in cases of bladder cancer.

It is also established that the endothelin receptor sub-type B is involved in the lack of recognition of some cancer cells, in particular of ovary cancer cells by the immune system, by inducing a strong reduction in the lymphocyte infiltration (Buckanovich et al, 2008, "Endothelin B receptor mediates the endothelial barrier to T cell homing to tumors and disables immune therapy", Nature Medecine, vol. 14, pages 28-36).

Thus, targeting an ETB-R conformational isomer expressed at the surface of cancer cells and in particular glioblastoma cells thereby appears particularly relevant in human clinical biology in terms of a diagnostic tool for the follow-up of the development of these tumors and in particular of these brain tumors and their recurrences after a surgical operation but also for therapeutic applications by targeting these tumor cells. Yet, in the passive immunotherapy arsenal of cancers using monoclonal antibodies (40 antibodies have been approved to date), none of them targets GPCRs.

Generally, few antibodies targeting endothelin receptors and in particular sub-type ETB-R are described to date.

Kondoh et al, 1990 ("Isolation of anti-endothelin receptor monoclonal antibodies for use in receptor characterization", BBRC, vol. 172, pages 503-510) describe the binding properties of 4 monoclonal antibodies (A2, G9, E7 and G10) to solubilised complexes of endothelin receptors present at the surface of rat lung membranes. Antibodies G9 and G10 are type G isotype 2a immunoglobulins (IgG2a), whereas antibodies A2 and E7 are IgG1 immunoglobulins. If these 4 antibodies are actually specific to solubilised endothelin receptors, Kondoh et al do not provide any information about the fine specificity of these antibodies (ETA-R and/or ETB-R), as regards the recognition of human origin receptors, nor as regards a possible antagonistic property.

Yamaguchi et al, 2004 ("Characterization and application of monoclonal antibodies against human endothelin B receptor expressed in insect cells", Biotechnology Letters, vol. 26, pages 293-299) relate to the characterization of the binding properties of 5 mouse monoclonal antibodies obtained after protein immunisation with recombinant human ETB-R produced in insect cells. Four of them have a similar affinity (in the nanomolar range) for ETB-R, whereas the fifth one is 10 times less affine. The epitopic analysis of 3 of them (N-6, N-3 and N-1) revealed that they recognise the ETB-R N-terminal domain and more particularly the sequence corresponding to amino acids 27-35 of the ETB-R for N-6; the sequence corresponding to amino acids 27-41 of the ETB-R for N-3 and the sequence corresponding to amino acids 71-85 for N-1. Finally, these 5 antibodies are capable of recognising COS cells over-expressing ETB-R.

Patent application US 2010/003240 deposited on behalf of New York University and published on the 7 Jan. 2010 relates to therapeutic protocols and pharmaceutical mixtures within the scope of the treatment and prevention of cancers and in particular melanomas. To that end and more specifically, the use of ETB-R antagonists is claimed. The examples described about these antagonists only relate to modified endothelin-1 forms, but by extension, the use of ETB-R antagonist antibodies is claimed whereas no particular example of such antibodies is described or provided.

Patent application JP 2012111706 on behalf of Seikisui Chemical Co Ltd and published on the 14 Jun. 2012 relates to a monoclonal antibody called hB07. This is an IgG2a/lambda isotype mouse immunoglobulin, which is specific to the endothelin receptor human sub-type B. The authors have shown that the antibody hB07 is capable of competitively blocking endothelin 1 binding with an efficiency ($IC_{50}$) calculated of $1.7 \cdot 10^{-7}$ M. This antibody the sequences of which are not described thus has antagonistic properties.

Likewise, a monoclonal antibody antagonist to the pharmacological properties of the endothelin receptor sub-type B and in particular human sub-type B, called Rendomab-B1 has been described in International application WO 2012/045776 on behalf of CEA and published on the 12 Apr. 2012.

Finally, International application WO 2013/063001 on behalves of Genentech and Hoffmann-La Roche and published on the 2 May 2013 describes a therapeutic antibody conjugated to cytotoxic molecules for the treatment of melanomas, without reference to a conformational isomer preferentially expressed by the tumor cells. This antibody called 5E9 targets the human ETB-R over-expressed at the surface of melanomas. It is to be noted that the antibody 5E9 crosses with the rodent ETB-R as well as the non-human primate receptor as is set out in Asundi et al, 2011 ("An antibody-drug conjugate targeting the endothelin B receptor for the treatment of melanoma", Clinical Cancer Research, vol. 17, pages 965-975).

The inventors thus set themselves the purpose to obtain antibodies able to target particular conformational isomers of the endothelin receptor sub-type B expressed at the surface of cancer cells.

DISCLOSURE OF THE INVENTION

The present invention enables technical problems such as those previously defined to be solved and the purpose set by the inventors to be reached.

In fact, the inventors have developed and used a particular selection immunisation strategy already published in Allard et al, 2011 ("Electroporation-aided DNA immunization generates polyclonal antibodies against the native conformation of human endothelin B receptor", DNA and Cell Biology, vol. 30, pages 727-737). This strategy coupled with a hybridoma screening procedure in ELISA-cell and then by flow cytometry favours the obtention of monoclonal antibodies specific to ETB-R in its native conformation. This approach further has the advantage not to need the extracted and purified receptor of interest, which is still today particularly challenging.

By this strategy, the inventors have been able to select different monoclonal antibodies directed against the endothelin receptor sub-type B and in particular the human sub-type B, called hereinafter Rendomab-B49, Rendomab-B41 and Rendomab-B36. These antibodies are not only close to each other as regards their nucleotide and peptide sequences but also as regards their properties. Thus, none of these antibodies is an antagonist to the pharmacological properties of the endothelin receptor sub-type B (ETB-R). In other words, the antibodies according to the present invention are not capable of inhibiting or blocking binding of the endothelin ligands and in particular ligands ET1, ET2 and ET3 on ETB-R. On the contrary, the antibodies according to the present invention are capable of recognising the particular conformational isomers of the endothelin receptor sub-type B expressed at the surface of cancer cells and in particular glioblastoma cells.

The present invention relates to an antibody directed against the endothelin receptor sub-type B, a fragment or derivative thereof.

Before describing the invention in further detail, the following definitions will be reminded or suggested.

The terms "antibody" and "immunoglobulin" are equivalent and can be used interchangeably in the present invention.

An antibody is a glycoprotein comprising at least two heavy chains (H) and at least two light chains (L) connected to each other by one or more disulphide bridges. Each heavy chain comprises a variable region (or domain) (VH) and a constant region comprising 3 domains, usually designated CH1, CH2 and CH3. Each light chain comprises a variable region (or domain) (VL) and a constant region comprising a single domain, usually designated CL. The variable regions of the heavy chains and light chains involved in the antigen recognition can be further subdivided into 3 hypervariable regions, also called "complementarity determining regions" (CDR), surrounded by 4 more conserved regions, also called framework regions (FR). The organisation of each heavy chain (or light chain) variable region is, from the N-terminal end to the C-terminal end, as follows: FR1, CDR1, FR2, CDR2, FR3, CDR3 and FR4. Within the scope of the present invention, the definition of CDRs and FRs which has been used is that of IMGT (the international ImMunoGeneTics database http://imgt.cines.fr:8104). The calculations of identity percents of the CDR sequences mentioned and claimed hereinafter are thus to be taken into account based on this annotation.

Furthermore, the term "antibody" includes, within the scope of the present invention, not only full antibody molecules but also fragments and derivatives thereof.

By "antibody fragment", it is meant, within the scope of the present invention, both a monovalent fragment which has a single antigen-binding site as well as a divalent fragment which has two antigen-combining sites. Thus, a fragment according to the invention has at least one antigen-binding site. Among these fragments, fragments Fab, F(ab')$_2$, Fv, and other fragments which conserve the antigen-binding site (scFv and diabody) can be mentioned. A fragment Fab is a monovalent fragment consisting of the full light chain and part of the heavy chain (Fd) comprising the domains VH and CH1 as previously defined. A fragment F(ab')$_2$ is a divalent fragment corresponding to the association of two fragments Fab connected by disulphide bridges present at the hinge region of the immunoglobulins located between the constant domains CH1 and CH2. A fragment Fv is a monovalent fragment only consisting of the variable regions VL and VH of the light and heavy chains of an antibody. A fragment scFv is a monovalent polypeptide fragment, only obtained by genetic engineering, corresponding to the variable domains connected by a peptide link. A diabody is a recombinant divalent antibody molecule consisting of two head to tail scFv molecules because of the too short peptide link to enable a scFv to be formed. The fragments according to the invention also cover fragments as previously mentioned the half-life of which has been increased by chemical modification in particular by incorporation in a liposome or introducing a polyalkylene glycol such as a polyethylene glycol (PEG), this technique being called "PEGylation" and giving fragments such as Fab-PEG, F(ab')$_2$-PEG or Fv-PEG. By recombinant route, it is also possible to generate single or fused fragments of the antibody according to the present invention, having more efficient and better controlled properties of penetrability of solid tumors and pharmacokinetics. The antibody fragments useful within the scope of the present invention can be natural or recombinant.

By "antibody derivative", it is meant, within the scope of the present invention, antibody fragments obtained by genetic engineering such as single chain Fv (scFv) and single domain antibody (dAb) molecules. The term also includes antibody type molecules which can be introduced using phage display techniques or other random selection techniques for molecules which bind to the endothelin receptor sub-type B or to regions specific to this sub-type.

Thus, the "antibody fragments" and "antibody derivatives" cover all the molecules which contain an advantageously peptide structure, which is part of the recognition site (that is the part of the antibody which binds to or combines to the epitope or antigen) of an antibody according to the present invention. In addition, the antibody fragments and derivatives according to the present invention are capable of recognising particular conformational isomers of the endothelin receptor sub-type B expressed at the surface of cancer cells and in particular glioblastoma cells.

The present invention relates to an antibody directed against the endothelin receptor sub-type B comprising:
a heavy chain variable region comprising a CDR1 (hereinafter designated $CDR1_H$), a CDR2 (hereinafter designated $CDR2_H$) and a CDR3 (hereinafter designated $CDR3_H$) such that the ordered juxtaposition formed by the amino acid sequences of the $CDR1_H$, $CDR2_H$ and $CDR3_H$ exhibits at least 80% identity with the following amino acid sequence: GYTFISY-WIDPDSGGTAREGDYAWFAY (SEQ ID NO: 1) and
a light chain variable region comprising a CDR1 (hereinafter designated $CDR1_L$), a CDR2 (hereinafter designated $CDR2_L$) and a CDR3 (hereinafter designated $CDR3_L$) such that the ordered juxtaposition formed by the amino acid sequences of the $CDR1_L$, $CDR2_L$ and $CDR3_L$ exhibits at least 80% identity with the following amino acid sequence: QSIVHSNGN-TYKVSFQGSHVPWT (SEQ ID NO: 2).

Within the scope of the present invention, the amino acid sequences are given in accordance with the 1-letter international code.

By "ordered juxtaposition formed by the amino acid sequences of the $CDR1_H$, $CDR2_H$ and $CDR3_H$ (or by the amino acid sequences of the $CDR1_L$, $CDR2_L$ and $CDR3_L$)", it is meant the artificial amino acid (aa) sequence having the following formula:

aa sequence of the $CDR1_H$+aa sequence of the $CDR2_H$+aa sequence of the $CDR3_H$ (or aa sequence of the $CDR1_L$+aa sequence of the $CDR2_L$+aa sequence of the $CDR3_L$).

Typically, the ordered juxtaposition formed by the amino acid sequences of the $CDR1_H$, $CDR2_H$ and $CDR3_H$ has at least 81% identity with the amino acid sequence SEQ ID NO: 1. Further, the ordered juxtaposition formed by the amino acid sequences of the $CDR1_L$, $CDR2_L$ and $CDR3_L$ has at least 85% identity with the amino acid sequence SEQ ID NO: 2.

Advantageously, the antibody according to the present invention comprises a heavy chain variable region the $CDR1_H$ of which has the following consensus sequence: $GYTFX_1SYW$ (SEQ ID NO: 3) in which $X_1$ represents any amino acid. In a particular embodiment, $X_1$ is either I, or T and the amino acid sequence of the $CDR1_H$ of the heavy chain variable region of the antibody according to the present invention is either GYTFISYW (SEQ ID NO: 5), or GYTFTSYW (SEQ ID NO: 7).

Further advantageously, the antibody according to the present invention comprises a heavy chain variable region the $CDR2_H$ of which has the following consensus sequence: $IDPX_2SGGT$ (SEQ ID NO: 8) in which $X_2$ represents any amino acid. In a particular embodiment, $X_2$ is either D, or N and the amino acid sequence of the $CDR2_H$ of the heavy chain variable region of the antibody according to the present invention is either IDPDSGGT (SEQ ID NO: 10), or IDPNSGGT (SEQ ID NO: 12).

Further advantageously, the antibody according to the present invention comprises a heavy chain variable region the $CDR3_H$ of which has the following consensus sequence: $X_3REGX_4X_5AWFX_6Y$ (SEQ ID NO: 13) wherein $X_3$, $X_4$, $X_5$ and $X_6$, being identical or different, represent any amino acid. In a particular embodiment, $X_3$, $X_4$, $X_5$ and $X_6$, being identical or different, are chosen from the group consisting of A, D, Y, E, F, V and W. In a more particular embodiment, $X_3$ is either A, or V; $X_4$ is chosen from the group consisting of D, W and E; $X_5$ is chosen from the group consisting of Y, D and F and $X_6$ is either A, or V. In a further more particular embodiment, the amino acid sequence of the $CDR3_H$ of the heavy chain variable region of the antibody according to the present invention is chosen from the group consisting of AREGDYAWFAY (SEQ ID NO: 15), VREGWDAWFVY (SEQ ID NO: 17) and AREGEFAWFAY (SEQ ID NO: 19).

Advantageously, the antibody according to the present invention comprises a light chain variable region the $CDR1_L$ of which has the following consensus sequence: $QX_7IVHSNGX_8TY$ (SEQ ID NO: 20) wherein $X_7$ and $X_8$, being identical or different, represent any amino acid. In a particular embodiment, $X_7$ and $X_8$, being identical or different, are chosen from the group consisting of N, Y and S. In a more particular embodiment, $X_7$ is either N, or S and $X_8$ is either N, or Y. In a further more particular embodiment, the amino acid sequence of the $CDR1_L$ of the light chain variable region of the antibody according to the present invention is either QSIVHSNGNTY (SEQ ID NO: 22), or QNIVHSNGYTY (SEQ ID NO: 24).

Further advantageously, the antibody according to the present invention comprises a light chain variable region the $CDR2_L$ of which has the following consensus sequence: $KVX_9$ wherein $X_9$ represents any amino acid. In a particular embodiment, $X_9$ is either S, or F and the amino acid sequence of the $CDR2_L$ of the light chain variable region of the antibody according to the present invention is either KVS, or KVF.

Further advantageously, the antibody according to the present invention comprises a light chain variable region the $CDR3_L$ of which has the following consensus sequence: $FQGSHVPX_{10}T$ (SEQ ID NO: 25) wherein $X_{10}$ represents any amino acid. In a particular embodiment, $X_{10}$ is either W, or L and the amino acid sequence of the $CDR3_L$ of the light chain variable region of the antibody according to the present invention is either FQGSHVPWT (SEQ ID NO: 27), or FQGSHVPLT (SEQ ID NO: 29).

Advantageously, the antibody according to the present invention comprises:
$i_1$) a heavy chain variable region comprising:
a $CDR1_H$ the amino acid sequence of which is GYTFI-SYW (SEQ ID NO: 5);
a $CDR2_H$ the amino acid sequence of which is IDPDSGGT (SEQ ID NO: 10); and
a $CDR3_H$ the amino acid sequence of which is AREGDYAWFAY (SEQ ID NO: 15);
or
$ii_1$) a heavy chain variable region comprising:
a $CDR1_H$ the amino acid sequence of which is GYTFT-SYW (SEQ ID NO: 7);
a $CDR2_H$ the amino acid sequence of which is IDPDSGGT (SEQ ID NO: 10); and
a $CDR3_H$ the amino acid sequence of which is VREGWDAWFVY (SEQ ID NO: 17);
or
$iii_1$) a heavy chain variable region comprising:
a $CDR1_H$ the amino acid sequence of which is GYTFT-SYW (SEQ ID NO: 7);
a $CDR2_H$ the amino acid sequence of which is IDPNSGGT (SEQ ID NO: 12); and a CDR3$_H$ the amino acid sequence of which is AREGE-FAWFAY (SEQ ID NO: 19).

More particularly, the antibody according to the invention comprises a heavy chain variable region the amino acid sequence of which exhibits at least 80% identity with the following sequence:

(SEQ ID NO: 31)
QVQLQQPGAALVKPGASVKLSCKASGYTFISYWMLWVKQRPGRGLEWIGR

IDPDSGGTKYNEKFKSKATLTVDKSSSTAYMQLSSLTSEDSAVYYCAREG

DYAWFAYWGQGTLVPVSA.

Thus, the antibody according to the invention comprises a heavy chain variable region the amino acid sequence of which exhibits at least 80% identity and can exhibit at least 81%, at least 82%, at least 83%, at least 84%, at least 85%, at least 86%, at least 87%, at least 88%, at least 89%, or even at least 90% identity with the amino acid sequence SEQ ID NO: 31.

Further more particularly, the antibody according to the invention comprises a heavy chain variable region the amino acid sequence of which corresponds to, i.e. consists of, the amino acid sequence SEQ ID NO: 31 (case of Rendomab-B49).

Alternatively (case of Rendomab-B41), the antibody according to the invention comprises a heavy chain variable region the amino acid sequence of which corresponds to, i.e. consists of, the following amino acid sequence:

(SEQ ID NO: 33)
QVQLQQPGAELVKPGASVKLSCKASGYTFTSYWMHWVKQRPGRGLEWIGR

IDPDSGGTKYNEKFKSKATLTVDKPSNTANMQLSSLTSEDSAVYYCVREG

WDAWFVYWGQGTLLTVSA.

In another alternative (case of Rendomab-B36), the antibody according to the invention comprises a heavy chain variable region the amino acid sequence of which corresponds to, i.e. consists of, the following amino acid sequence:

(SEQ ID NO: 35)
QVQLQQPGAELVKPGASVKLSCKASGYTFTSYWIHWVNQRPGRGLEWIGR

IDPNSGGTKYNEKFKSKATLTVDKTSSTAYMQFSSLTSEDSAVYYCAREG

EFAWFAYWGQGTLVTVSA.

Advantageously, the antibody according to the present invention comprises:

i$_2$) a light chain variable region comprising:
  a CDR1$_L$ the amino acid sequence of which is QSIVHSNGNTY (SEQ ID NO: 22);
  a CDR2$_L$ the amino acid sequence of which is KVS;
  a CDR3$_L$ the amino acid sequence of which is FQGSHVPWT (SEQ ID NO: 27);
or
ii$_2$) a light chain variable region comprising:
  a CDR1$_L$ the amino acid sequence of which is QSIVHSNGNTY (SEQ ID NO: 22);
  a CDR2$_L$ the amino acid sequence of which is KVF;
  a CDR3$_L$ the amino acid sequence of which is FQGSHVPLT (SEQ ID NO: 29);
or
iii$_2$) a light chain variable region comprising:
  a CDR1$_L$ the amino acid sequence of which is QNIVHSNGYTY (SEQ ID NO: 24);
  a CDR2$_L$ the amino acid sequence of which is KVS;
  a CDR3$_L$ the amino acid sequence of which is FQGSHVPLT (SEQ ID NO: 29).

More particularly, the antibody according to the invention comprises a light chain variable region the amino acid sequence of which exhibits at least 80% identity with the following sequence:

(SEQ ID NO: 37)
DVLMTQTPLSLPVSLGDQASISCRSSQSIVHSNGNTYLEWYLQKPGQSPK

LLIYKVSNRFSGVPDRFSGSGSGTDFTLKISRVEAEDLGVYYCFQGSHVP

WTFGGGTKLEIK.

Thus, the antibody according to the invention comprises a light chain variable region the amino acid sequence of which exhibits at least 80% identity and can exhibit at least 81%, at least 82%, at least 83%, at least 84%, at least 85%, at least 86%, at least 87%, at least 88%, at least 89%, at least 90%, at least 91%, at least 92%, at least 93%, at least 94% or even at least 95% identity with the amino acid sequence SEQ ID NO: 37.

Further more particularly, the antibody according to the invention comprises a light chain variable region the amino acid sequence of which corresponds to, i.e. consists of, the amino acid sequence SEQ ID NO: 37 (case of Rendomab-B49).

Alternatively (case of Rendomab-B41), the antibody according to the invention comprises a light chain variable region the amino acid sequence of which corresponds to, i.e. consists of, the following amino acid sequence:

(SEQ ID NO: 39)
DVLMTQTPLSLPVSLGDQASISCRSSQSIVHSNGNTYLEWYLQKPGQSPK

LLIYKVFNRFSGVPDRFSGSGSGTDFTLKISRVEAEDLGVYYCFQGSHVP

LTFGAGTKLELKR.

In another alternative (case of Rendomab-B36), the antibody according to the invention comprises a light chain variable region the amino acid sequence of which corresponds to, i.e. consists of, the following amino acid sequence:

(SEQ ID NO: 41)
DVLMTQTPLSLPVSLGDQASISCRSSQNIVHSNGYTYLEWYLQKPGQSPK

LLIYKVSNRFSGVPDRFSGSGSGTDFTLKISRVEAEDLGVYYCFQGSHVP

LTFGSGTKLEIKR.

Advantageously, the antibody according to the invention comprises a light chain variable region and a heavy chain variable region such as previously defined.

The light chain of the antibody according to the invention is typically a kappa light chain.

The heavy chain of the antibody according to the invention is in particular a gamma 1 heavy chain or a gamma 3 heavy chain.

In particular, the antibody according to the present invention is a G type immunoglobulin.

More particularly, the antibody according to the present invention is an IgG1/kappa type or IgG3 kappa type immunoglobulin.

The antibody directed against the endothelin receptor sub-type B, which is the subject matter of the present invention, selectively binds extracellular segments of the ETB-R. By "antibody which selectively binds" at least one specified domain or region of the ETB-R in particular of the human ETB-R, it is meant, within the scope of the present invention, an antibody which binds the specific domain(s) with a greater affinity than any other region of the ETB-R. Advantageously, the antibody binds the specified domain(s) of the ETB-R with an affinity at least 2, or at least 5, or at least 10, or at least 50 times higher than that it exhibits for any other region of the ETB-R. This binding can be determined by well-known processes in the field such as flow cytometry, radio-immuno-assay (RIA), confocal microscopy, enzyme-immuno-assay (EIA) labelling by directly or indirectly revealing the antibody to be tested (ELISA).

The antibody which is the subject matter of the present invention can be obtained from an animal immunised against the endothelin receptor sub-type B or against a fragment of this receptor comprising the epitope(s) recognised by the antibody according to the present invention. The immunised animal can be any animal usually used for producing an antibody such as a mouse, rat, rabbit, goat, dog, horse or camelid such as a camel or lama.

The antibody which is the subject matter of the present invention can also be obtained from naive recombinant (scFv, Fab, . . . ) libraries expressed at the surface of virus, phages, bacteria, yeasts or other eukaryotic cells, these libraries being built from immunoglobulins of different immunized animals as above disclosed.

The antibody thus obtained can be purified on an affinity column on which the endothelin receptor sub-type B or one of the sequences specifically recognised by the antibody according to the invention has been immobilised beforehand. This purification can also involve a protein A affinity chromatography.

Within the scope of the present invention, the antibody can be a polyclonal polyspecific or monospecific antibody, or a monoclonal antibody.

Advantageously, the antibody of the present invention is monoclonal. A "monoclonal antibody" refers, by usual definition in immunology, to an antibody obtained from a population of substantially homogenous antibodies, i.e. a population of identical antibodies, and a relatively low amount of the same can have possibly a mutation. A monoclonal antibody is obtained from the proliferation of a single clone of cells such as a hybridoma.

More particularly, the antibody according to the present invention is the murine monoclonal antibody obtained from a hybridoma chosen from the hybridoma deposited with the Collection Nationale des Cultures des Microorganismes (CNCM) on the 19 May 2016 under the accession number CNCM I 5084 (Rendomab-B49), the hybridoma deposited with the CNCM on the 7 Jun. 2016 under the accession number CNCM I-5104 (Rendomab-B41) and the hybridoma deposited with the CNCM on the 7 Jun. 2016 under the accession number CNCM I-5103 (Rendomab-B36). All restrictions imposed by the depositor on the availability to the public of these deposited materials will be irrevocably removed upon granting of a patent. The present invention also relates to such hybridomas.

Alternatively, the antibody according to the present invention can be a chimeric antibody i.e. an antibody which contains variable regions or hypervariable regions of heavy and light chain(s) derived from an antibody of a given species in combination with the constant regions of heavy and light chain(s) derived from an antibody of another species heterologous to the previous one.

A first alternative of the present invention corresponds to a chimerized antibody and in particular a chimerized monoclonal antibody, that is an antibody whose previously described variable domains from the murine antibody are associated with constant domains of human origin. It should be reminded that several therapeutic antibodies in use in humans are chimerized antibodies.

A second particularly interesting alternative can be a humanized antibody and in particular a humanized monoclonal antibody. Indeed, it is preferable to use a humanized antibody, if the latter should be administrated repeatedly to a human subject.

In the case of a humanized monoclonal antibody according to the present invention, the latter could be prepared by inserting CDRs of a murine antibody and in particular the murine antibody from a hybridoma chosen from the hybridoma deposited with the Collection Nationale de Cultures de Microorganisms (CNCM) on the 19 May 2016 under the accession number CNCM 1-5084 (Rendomab-B49), the hybridoma deposited with the CNCM on the 7 Jun. 2016 under the accession number CNCM I-5104 (Rendomab-B41) and the hybridoma deposited with the CNCM on the 7 Jun. 2016 under the accession number CNCM I-5103 (Rendomab-B36) within a human antibody, regardless of its isotype (IgG, IgA, IgM). All restrictions imposed by the depositor on the availability to the public of these deposited materials will be irrevocably removed upon granting of a patent. The humanized antibodies can be made using techniques and approaches described in Verhoeyen et al, 1988 ("Reshaping human antibodies: Grafting an antilysozyme activity", Science, vol. 239, pages 1534-1536) and in U.S. Pat. No. 4,816,567 on behalf of Genentech and published on the 28 Mar. 1989.

The antibodies can also be human antibodies in that they have the amino acid sequence of anti-ETB-R human antibodies via preparation processes known in the field which do not require human vaccination. For example, such antibodies can be obtained by gene immunisation/cell immunisation boosts of transgenic mice which are available and which contain in essence human immunoglobulin genes (see Vaughan et al, 1998, "Human antibodies by design", Nature Biotechnol. vol. 16, pages 535-539). Alternatively, such antibodies can be obtained by cloning CDNAs coding from human B lymphocytes directed against ETB-R.

The present invention also relates to isolated polynucleotide chosen from the different polynucleotides hereinafter:

α) a polynucleotide encoding an antibody as previously defined;

β) a polynucleotide complementary to the polynucleotide as defined in (α);

γ) a polynucleotide of at least 18 nucleotides, capable of hybridising under high stringency conditions with the polynucleotides as defined in (α) and (β).

By "polynucleotide", it is meant, within the scope of the present invention, a nucleic acid, a nucleic sequence, a nucleic acid sequence, an oligonucleotide, a polynucleotide sequence, a nucleotide sequence, a single strand DNA, a double strand DNA or an RNA. A polynucleotide according to the present invention can comprise natural nucleotides and non-natural nucleotides.

The polynucleotide according to the invention does not correspond to a nucleotide sequence in its natural state i.e. in its natural chromosomal environment. On the contrary, the polynucleotide according to the invention has been isolated and possibly purified, its environment has consequently been modified. The polynucleotide according to the invention can also be obtained by genetic recombination or chemical synthesis.

The high stringency conditions correspond to temperature and ionic strength conditions which enable a hybridization to be maintained between two complementary nucleotide sequences. Those skilled in the art will be able to determine the most suitable high stringency conditions in particular depending on the size of the nucleotide sequences by referring to the teaching of Sambrook et al, 1989 (Molecular cloning, Noland C. ed., New York: Cold Spring Harbor Laboratory Press).

The polynucleotide according to the present invention comprises at least one nucleotide sequence coding the $CDR1_H$ chosen from the following nucleotide sequences:

```
                                        (SEQ ID NO: 4)
GGC TAC ACC TTC ATC AGC TAC TGG
and (SEQ ID NO: 6)
GGC TAC ACC TTC ACC AGC TAC TGG.
```

Advantageously, the polynucleotide according to the present invention comprises at least one nucleotide sequence coding the $CDR2_H$ chosen from the following nucleotide sequences:

```
                                        (SEQ ID NO: 9)
ATT GAT CCT GAT AGN₁ GGT GGT ACT with N₁
representing either C, or T
and (SEQ ID NO: 11)
ATT GAT CCT AAT AGT GGT GGC ACT.
```

Further advantageously, the polynucleotide according to the present invention comprises at least one nucleotide sequence coding the $CDR3_H$ chosen from the following nucleotide sequences:

```
                                        (SEQ ID NO: 14)
GCA AGA GAA GGG GAT TAC GCC TGG TTT GCT TAC;

(SEQ ID NO: 16)
GTA AGA GAA GGG TGG GAC GCC TGG TTT GTT TAC
and (SEQ ID NO: 18)
GCA AGA GAG GGG GAA TTC GCC TGG TTT GCT TAC.
```

Typically, the polynucleotide according to the present invention comprises at least one nucleotide sequence coding the $CDR1_L$ chosen from the following nucleotide sequences:

```
                                        (SEQ ID NO: 21)
CAG AGC ATT GTA CAT AGT AAT GGA AAC ACC TAT
and (SEQ ID NO: 23)
CAG AAC ATT GTC CAT AGT AAT GGA TAC ACC TAT.
```

In particular, the polynucleotide according to the present invention comprises at least one nucleotide sequence coding the $CDR2_L$ chosen from the following nucleotide sequences:

```
AAA GTT TCC
and

AAA GTT TTC.
```

More particularly, the polynucleotide according to the present invention comprises at least one nucleotide sequence coding the $CDR3_L$ chosen from the following nucleotide sequences:

```
                                        (SEQ ID NO: 26)
TTT CAA GGT TCA CAT GTT CCG TGG ACG
and (SEQ ID NO: 28)
TTT CAA GGT TCA CAT GTT CCN₂ CTC ACG with N₂
representing either G, or T.
```

Advantageously, the polynucleotide according to the present invention comprises at least three nucleotide sequences corresponding to one of the following groups:

(i₁') the nucleotide sequences SEQ ID NO: 4, SEQ ID NO: 9 with N₁ representing C and SEQ ID NO: 14;

(ii₁') the nucleotide sequences SEQ ID NO: 6, SEQ ID NO: 9 with N₁ representing T and SEQ ID NO: 16; and (iii₁') the nucleotide sequences SEQ ID NO: 6, SEQ ID NO: 11 with N₁ representing T and SEQ ID NO: 18.

It is clear that, for each of the groups, the three sequences listed above have to be organised with respect to each other such that the polypeptide obtained at the end of the translation of the polynucleotide according to the invention comprises 3 peptide sequences corresponding to the $CDR1_H$, $CDR2_H$ and $CDR3_H$.

More particularly, the polynucleotide according to the present invention comprises at least one nucleotide sequence having at least 80% identity with the following nucleotide sequence:

```
                                        (SEQ ID NO: 30)
CAGGTCCAACTGCAGCAGCCTGGGGCTGCGCTTGTGAAGCCTGGGGCTTC

AGTGAAGCTGTCCTGCAAGGCTTCTGGCTACACCTTCATCAGCTACTGGA

TGCTCTGGGTGAAGCAGAGGCCTGGACGAGGCCTTGAGTGGATTGGAAGG

ATTGATCCTGATAGCGGTGGTACTAAGTACAATGAGAAGTTCAAGAGCAA

GGCCACACTGACTGTAGACAAATCCTCCAGCACAGCCTACATGCAGCTCA

GCAGCCTGACATCTGAGGACTCTGCGGTCTATTATTGTGCAAGAGAAGGG

GATTACGCCTGGTTTGCTTACTGGGGCCAAGGGACTCTGGTCCCTGTCTC

TGCA.
```

Thus, the polynucleotide according to the present invention comprises at least one nucleotide sequence having at least 80% identity and can exhibit at least 81%, at least 82%, at least 83%, at least 84%, at least 85%, at least 86%, at least 87%, at least 88%, at least 89%, or even at least 90% identity with the nucleotide sequence SEQ ID NO: 30.

Further more particularly, the polynucleotide according to the present invention comprises a nucleotide sequence corresponding to the nucleotide sequence SEQ ID NO: 30 (case of Rendomab-B49). Thus, the nucleotide sequence coding the heavy chain variable region of Rendomab-B49 comprises or consists of the nucleotide sequence SEQ ID NO: 30.

Alternatively (case of Rendomab-B41), the polynucleotide according to the present invention comprises the following nucleotide sequence:

(SEQ ID NO: 32)
CAGGTCCAACTGCAGCAGCCTGGGGCTGAGCTTGTGAAGCCTGGGCTTC

AGTGAAGCTGTCCTGCAAGGCTTCTGGCTACACCTTCACCAGCTACTGGA

TGCACTGGGTGAAGCAGAGGCCTGGACGAGGCCTTGAGTGGATTGGAAGG

ATTGATCCTGATAGTGGTGGTACTAAATACAATGAGAAGTTCAAGAGCAA

GGCCACACTGACTGTAGACAAACCCTCCAACACAGCCAACATGCAGCTCA

GCAGCCTGACATCTGAAGACTCTGCGGTCTATTATTGTGTAAGAGAAGGG

TGGGACGCCTGGTTTGTTTACTGGGGCCAAGGGACTCTGCTCACTGTCTC

TGCA.

Thus, the nucleotide sequence coding the heavy chain variable region of Rendomab-B41 comprises or consists of the nucleotide sequence SEQ ID NO: 32.

In another alternative (case of Rendomab-B36), the polynucleotide according to the present invention comprises the following nucleotide sequence:

(SEQ ID NO: 34)
CAGGTCCAACTGCAGCAGCCTGGGGCTGAACTTGTGAAGCCTGGGCTTC

AGTGAAGCTGTCCTGCAAGGCTTCTGGCTACACCTTCACCAGCTACTGGA

TACACTGGGTAAATCAGAGGCCTGGACGAGGCCTTGAGTGGATTGGAAGG

ATTGATCCTAATAGTGGTGGCACTAAGTACAATGAGAAGTTCAAGAGTAA

GGCCACACTGACTGTAGACAAAACCTCCAGCACAGCCTACATGCAGTTCA

GCAGCCTGACATCTGAGGACTCTGCGGTCTATTATTGTGCAAGAGAGGG

GAATTCGCCTGGTTTGCTTACTGGGGCCAAGGGACTCTGGTCACTGTCTC

TGCA.

Thus, the nucleotide sequence coding the heavy chain variable region of Rendomab-B36 comprises or consists of the nucleotide sequence SEQ ID NO: 34.

Advantageously, the polynucleotide according to the present invention comprises at least three nucleotide sequences corresponding to one of the following groups:

($i_2'$) the nucleotide sequences SEQ ID NO: 21, AAAGTTTCC and SEQ ID NO: 26;

($ii_2'$) the nucleotide sequences SEQ ID NO: 21, AAAGTTTTC and SEQ ID NO: 28 with $N_2$ representing G; and ($iii_2'$) the nucleotide sequences SEQ ID NO: 23, AAAGTTTCC and SEQ ID NO: 28 with $N_2$ representing T.

It is clear that, for each of the groups, the three sequences listed above have to be organised with respect to each other such that the polypeptide obtained at the end of the translation of the polynucleotide according to the invention comprises 3 peptide sequences corresponding to the $CDR1_L$, $CDR2_L$ and $CDR3_L$.

More particularly, the polynucleotide according to the present invention comprises at least one nucleotide sequence having at least 80% identity with the following nucleotide sequence:

(SEQ ID NO: 36)
GATGTTTTGATGACCCAAACTCCACTCTCCCTGCCTGTCAGTCTTGGAGA

TCAAGCCTCCATCTCTTGCAGATCTAGTCAGAGCATTGTACATAGTAATG

GAAACACCTATTTAGAATGGTACCTGCAGAAACCAGGCCAGTCTCCAAAG

CTCCTGATCTACAAAGTTTCCAACCGATTTTCTGGGGTCCCAGACAGGTT

CAGTGGCAGTGGATCAGGGACAGATTTCACACTCAAGATCAGCAGAGTGG

AGGCTGAGGATCTGGGAGTTTATTACTGCTTTCAAGGTTCACATGTTCCG

TGGACGTTCGGTGGAGGCACCAAGCTGGAAATCAAA.

Thus, the polynucleotide according to the present invention comprises at least one nucleotide sequence exhibiting at least 81%, at least 82%, at least 83%, at least 84%, at least 85%, at least 86%, at least 87%, at least 88%, at least 89%, at least 90%, at least 91%, at least 92%, at least 93%, at least 94% or even at least 95% identity with the nucleotide sequence SEQ ID NO: 36.

Further more particularly, the polynucleotide according to the present invention comprises a nucleotide sequence corresponding to the nucleotide sequence SEQ ID NO: 36 (case of Rendomab-B49). Thus, the nucleotide sequence coding the light chain variable region of Rendomab-B49 comprises or consists of the nucleotide sequence SEQ ID NO: 36.

Alternatively (case of Rendomab-B41), the polynucleotide according to the present invention comprises the following nucleotide sequence:

(SEQ ID NO: 38)
GATGTTTTGATGACCCAAACTCCACTCTCCCTGCCTGTCAGTCTTGGAGA

TCAAGCCTCCATCTCTTGCAGATCTAGTCAGAGCATTGTACATAGTAATG

GAAACACCTATTTAGAATGGTACTTGCAGAAACCAGGCCAGTCTCCAAAG

CTCCTGATCTACAAAGTTTTCAACCGATTTTCTGGGGTCCCAGACAGGTT

CAGTGGCAGTGGATCAGGGACAGATTTCACACTCAAGATCAGCAGAGTGG

AGGCTGAGGATCTGGGAGTTTATTACTGCTTTCAAGGTTCACATGTTCCG

CTCACGTTCGGTGCTGGGACCAAGCTGGAGCTGAAACGG.

Thus, the nucleotide sequence coding the light chain variable region of Rendomab-B41 comprises or consists of the nucleotide sequence SEQ ID NO: 38.

In another alternative (case of Rendomab-B36), the polynucleotide according to the present invention comprises the following nucleotide sequence:

(SEQ ID NO: 40)
GATGTTTTGATGACCCAAACTCCACTCTCCCTGCCTGTCAGTCTTGGAGA

TCAAGCCTCCATCTCTTGCAGATCTAGTCAGAACATTGTCCATAGTAATG

GATACACCTATTTAGAATGGTACCTGCAGAAACCAGGCCAGTCTCCAAAG

CTCCTGATCTACAAAGTTTCCAACCGATTTTCTGGGGTCCCAGACAGGTT

CAGTGGCAGTGGATCAGGGACAGATTTCACACTCAAGATCAGCAGAGTGG

AGGCTGAGGATCTGGGAGTTTATTACTGCTTTCAAGGTTCACATGTTCCT

CTCACGTTCGGCTCGGGGACAAAGTTGGAAATAAAACGG.

Thus, the nucleotide sequence coding the light chain variable region of Rendomab-B36 comprises or consists of the nucleotide sequence SEQ ID NO: 40.

By "identity percent" between two amino acid sequences (or between two nucleotide sequences), it is meant, within the scope of the present invention, a percent of identical amino acid (or nucleotide) residues between the two sequences being compared, this percent being obtained after implementing the best alignment (optimum alignment)

between both sequences. Those skilled in the art know different techniques enabling such an identity percent to be obtained and involving homology algorithms or computer programs such as the program BLAST.

The identity percent is statistic and the differences between both sequences are randomly distributed along these sequences. The differences between both sequences can consist of different modification types of the sequences: deletions, substitutions or additions of amino acid (or nucleotide) residues.

In a 1$^{st}$ embodiment, the modifications implemented in the sequences result in substitutions between equivalent amino acids, i.e. amino acids having structural homologies or not substantially modifying the biological activity of the corresponding antibodies.

In a 2$^{nd}$ embodiment, the modifications implemented in the sequences result in substitutions by non-equivalent amino acids, i.e. amino acids not having a structural homology. These modifications are likely to improve the biological properties of the antibody, i.e. improved affinity and/or specificity, widened recognition spectrum, increased stability, reduced immunogenicity etc.

When applied to both previously set out embodiments, these modifications, insertions or deletions can target a CDR, which is essential or not, to the properties of the antibody according to the invention.

When applied to both previously set out embodiments, these modifications, insertions or deletions can also target a region FR, given that such regions, within variable domains of the antibodies, can depending on the antibodies also play a role in the expression of the properties of the antibody according to the invention.

The present invention also relates to a cloning and/or expression vector containing at least one polynucleotide according to the present invention. Such a vector is in particular useful to transform a host organism and express in the latter an antibody according to the present invention.

The vector according to the present invention further comprises one (or more) element(s) which enable(s) the polynucleotide according to the present invention to be expressed and/or the product resulting from the translation of the polynucleotide according to the present invention to be secreted. Among these elements, a constituent or inducible promoter, a transcription initiation signal or a transcription termination signal, a translation initiation sequence or a translation end signal can be mentioned.

Advantageously, the vector according to the present invention comprises a promoter, a polynucleotide of the invention and a terminator element which are operationally linked to each other. By "operationally linked to each other", according to the invention, it is meant elements linked to each other such that the functioning of one of the elements is affected by that of another one. By way of example, a promoter is operationally linked to a coding sequence when it is capable of affecting the expression of the same. The peptide transcription, translation and maturation regulating elements that the vector can comprise are known to those skilled in the art who are able to choose them depending on the host organism in which the expression or cloning should be made.

The vector according to the present invention is advantageously chosen from a plasmid, a cosmid, a bacteriophage and a virus such as a baculovirus. In particular, the vector of the invention is an autonomously replicating vector including elements enabling it to be maintained and replicated in the host organism as a replication origin. Further, the vector can include elements enabling it to be selected in the host organism as, for example, an antibiotic resistant gene or selection gene which ensures complementation with the respective gene deleted in the genome of the host organism. Such cloning and/or expression vectors are well known to those skilled in the art and widely described in the literature.

The invention also relates to a host organism transformed by or comprising a polynucleotide according to the present invention or a vector according to the present invention.

By "host organism", it is meant any isolated, single or multi-cell, lower or higher organism, in which a polynucleotide of the invention is introduced for producing an antibody according to the present invention.

Those skilled in the art know different methods for efficiently introducing a polynucleotide into a host organism in order to produce the antibody coded by said polynucleotide in the host organism. By way of example and in a non-exhaustive way, this method can be an electroporation, lipofection, biological transformation of a plant using *Agrobacterium tumefasciens*, a heat shock or a chemical process.

Advantageously, the host organism is a microorganism such as a yeast, bacterium or fungus. The transformation of such microorganisms enables the antibody of the invention to be produced at a semi-industrial or industrial scale.

Alternatively, the host organism is an animal cell such as mammal cell, plant cell, insect cell, animal except for a human, or a plant.

Such host organisms can be used to produce an antibody according to the present invention. Indeed, a process for producing an antibody according to the present invention comprises the following steps of:

a) culturing a host organism according to the present invention and in particular a single-cell host organism in a culture medium and under appropriate conditions;

b) recovering said antibody from the culture medium of said cultured host organism or from said cultured host organism.

The antibody according to the present invention is also modifiable in order to i) generate an antibody labelled by a radioactive isotope, by a prodrug, an enzyme or a toxin, and ii) modify the binding specificity and/or affinity, and/or stability, and/or immunogenicity of said antibody ensuring targeting of the cells which over-express ETB-R, in particular cancer cells such as melanomas, glioblastomas etc. . . . .

The antibody according to the present invention is also modifiable in order to couple it chemically or genetically to a peptide molecule; a protein molecule; a nucleic molecule such as a DNA, an RNA, an RNAi, an aptamer, a PNA or an LNA; a lipid molecule; a carbohydrate molecule or a chemical molecule.

The present invention thus relates to a compound comprising an antibody according to the present invention conjugated with an element chosen from the group consisting of a cytotoxic group, an easily detectable group or an effector group.

By "cytotoxic group", it is meant a group directly or indirectly toxic for the cells targeted by the antibody according to the present invention. By "directly cytotoxic", it is meant a group which is cytotoxic on its own. By "indirectly cytotoxic", it is meant a group which, although not cytotoxic on its own, can induce a cytotoxicity, for example by its action on another molecule or by a further action on itself.

In a 1$^{st}$ implementation form, the cytotoxic group is a cytotoxic chemotherapeutic agent. Those skilled in the art know different cytotoxic chemotherapeutic agents usable within the scope of the present invention. The activity of these agents can be increased under irradiation. By way of illustrating and non-limiting examples, alkylating agents such as mechlorethamine or chlorambucile; methotrexate; 5-fluoro-uracil; vinblastine; gemcitabine; fludarabine; nicotinamide; doxorubicin; mitomycin; L-asparaginase; cisplatin; taxol and analogues/derivatives thereof can be mentioned.

In a $2^{nd}$ implementation form, the cytotoxic group is a cytotoxic (poly)peptide group such as ricin, abrin, *Pseudomonas* exotoxin, TNFα and interleukin 2.

In a $3^{rd}$ implementation form, the cytotoxic group is an indirectly cytotoxic chemotherapeutic agent. Such an agent also called a prodrug is little or not cytotoxic as such but is able to give, in particular after an enzymatic reaction or an irradiation, a cytotoxic substance (or drug) in particular as defined in the $1^{st}$ implementation form. By way of illustrating and non-limiting examples, methotrexate-alanine; mitomycin phosphate, 5-fluorocytosine; photofrin and capecitabine can be mentioned.

In a $4^{th}$ implementation form, the cytotoxic group is an indirectly cytotoxic (poly)peptide group. By indirectly cytotoxic polypeptide group, it is meant a peptide or polypeptide which exhibits an enzymatic activity and can convert a relatively non toxic prodrug in particular as defined in the $3^{rd}$ implementation form into a cytotoxic substance in particular as defined in the $1^{st}$ implementation form. Among such indirectly cytotoxic (poly)peptide groups, a peptidase such as a carboxypeptidase, aminopeptidase or endopeptidase; a phosphatase; a sulphatase; an amidase; a kinase; a glycosidase; a deaminase; a reductase; and an oxidase can be mentioned.

In a $5^{th}$ implementation form, the cytotoxic group is a nucleic acid molecule which is directly or indirectly cytotoxic such as an anti-sense oligonucleotide or an aptamer.

Those skilled in the art know different techniques enabling such groups to be conjugated with an antibody according to the present invention once the latter is obtained or produced.

These techniques allow a covalent coupling between an antibody according to the invention and a cytotoxic group by taking advantage of particular chemical groups carried by the antibody according to the invention and by the cytotoxic group. Among these particular chemical groups, a thiol group, an ester group, an amino group, an acid group and any chemical element likely to be implemented in "click-chemistry" can be mentioned.

Alternatively and in particular when the cytotoxic group is a group of peptidic nature, this conjugation can consist in producing the compound according to the invention as a fusion compound by genetic recombination techniques, wherein a polynucleotide comprises respective regions coding the antibody according to the present invention and the cytotoxic group, which are adjacent to each other, juxtaposed or separated by a region coding a peptide linker which does not destroy the desired properties of the final hybrid compound.

Irrespective of the technique used to conjugate an antibody according to the present invention with a cytotoxic group, the only requirement to meet within the scope of this conjugation is that the conjugated antibody preserves its ETB-R binding specificity and its absence of antagonist properly, which properties are associated to those of the cytotoxic group.

By "easily detectable group", it is meant, within the scope of the present invention, a group that can be detected by implementing an advantageously non-invasive appropriate detection technique such as microscopy, scintigraphy, positon emission tomography (TEP) and magnetic resonance imaging (MRI). A compound according to the invention comprising such an easily detectable group is particularly suitable for the field of imaging and diagnosis. It enables in particular sites at which the ETB-R is over-expressed to be identified and localised because of the ETB-R binding specificity of the antibody according to the invention present in this compound.

In a $1^{st}$ implementation form, the easily detectable group can be an enzyme or a molecule capable of generating a detectable and possibly quantifiable signal under particular conditions such as when putting into contact with an adapted substrate. By way of illustrating and non-limiting examples, biotin, digoxigenin, 5-bromodeoxiuridin, an alkaline phosphatase, a peroxidase, an acetylcholine esterase (AChE), a glucose amylase and a lysozyme can be mentioned.

In a $2^{nd}$ implementation form, the easily detectable group can be a fluorescent, chemiofluorescent or bioluminescent label such as fluorescein and derivatives thereof, rhodamine and derivatives thereof, GFP (Green Fluorescent Protein) and derivatives thereof and umbelliferone; luminol; luciferase and luciferin.

In a $3^{rd}$ implementation form, the easily detectable group can be a radioactive label or isotope such as iodine-123, iodine-125, iodine-126, iodine-133, indium-111, indium-113m, bromine-77, gallium-67, gallium-68, ruthenium-95, ruthenium-97, technetium-99m, fluorine-19, fluorine-18, carbon-13, nitrogen-15, oxygen-17, scandium-47, tellurium-122m, thulium-165 and yttrium-199. It should be observed that some radioactive atoms used as easily detectable groups can also be cytotoxic groups because of the radioactivity quantity they can deliver.

All that has been previously explained for the conjugation of the antibody according to the invention with cytotoxic groups is applicable mutatis mutandis to the conjugation of the antibody according to the invention with the easily detectable groups. The conjugation of the antibody according to the invention with the easily detectable groups can also be made in connection with nano-objects, in order to densify the concentration thereof, and thus to improve the emitted signal, contrast or toxicity.

In the case where this easily detectable group is a radioactive label, the latter can be introduced into the peptide sequence of the antibody according to the invention. This introduction can take place during the synthesis of the antibody by using one or more labelled amino acids. Alternatively, this introduction can take place following this synthesis by binding the radioactive label on residues of the peptide sequence of the synthesized antibody. For example, yttrium-90 can be bound via a lysine residue. Further alternatively, the radioactive label can be indirectly bound to the antibody by known means. For example, EDTA or another chelating agent can be bound to the antibody according to the invention and used to bind indium-111.

The present invention relates to the use of a compound comprising an antibody and an easily detectable group as a very efficient diagnostic, prognostic and in vivo follow up tool in terms of medical imaging. The antibody format is chosen so as to generate the best signal to noise ratio and the best pharmaco kinetics.

In other words, the present invention relates to a process for detecting and quantifying in vivo or in vitro the expression or overexpression of the endothelin receptor sub-type B, consisting in:

$a_1$) contacting a biological sample with a compound according to the present invention;

$b_1$) detecting the possible complex between said compound and said endothelin receptor sub-type B.

Such a process can be implemented to detect, diagnose, prognose or follow up a state in which the endothelin receptor sub-type B is overexpressed and in particular to detect, diagnose, prognose or follow up a cancer state (presence, size and evolution of cancer tumors). In the case of a process for diagnosing a cancer such as a glioblastoma, the latter comprises the steps of:

$a_1'$) contacting a biological sample of the subject with a compound according to the present invention;

$b_1'$) detecting the signal emitted by the easily detectable group and $c_1'$) determining the presence or absence of a cancer in said subject based on the signal detected in step ($b_1'$).

In a particular embodiment, the diagnostic process according to the invention is a process made in vitro for which the biological sample such as a biopsy has been taken from the subject before implementing step ($a_1'$). Alternatively, this process can correspond to an in vivo imaging process in which an efficient amount of the compound according to the invention has been administrated to the subject beforehand. By "efficient amount", it is meant an amount of the compound according to the present invention which is sufficient for cancer imaging. This amount varies as a function of the administration mode, the formulation administrated, the excipient and the cancer to be diagnosed. However, determining this efficient amount is a routine work for those skilled in the art.

By "effector group", it is meant, within the scope of the present invention, a group capable of specifically recognising a cancer marker, or which makes it possible to recruit (i) an effector cell of the immune system i.e. NK cells, cytotoxic T cells, macrophages or (ii) the complement system. By "group capable of specifically recognising a cancer marker", it is meant, within the scope of the present invention, a ligand of a cancer marker; an antibody identical to or different from the antibody according to the present invention; a protein; a peptide; or a nucleic molecule such as a DNA, an RNA, an RNAi, an aptamer, a PNA or an LNA. By "cancer label", both an ETB-R and another membrane marker are contemplated.

In a $1^{st}$ implementation form, the effector group recognises a cancer marker which is, identical to or different from ETB-R, expressed at the surface of cancer cells, thus ensuring better recognition specificity and thus increased targeting of cancer cells.

In a $2^{nd}$ implementation form, the effector group exhibits a recognition specificity for a marker specifically present at the surface of effector cells of the immune system, i.e. NK cells, macrophages or cytotoxic T cells. Such a recruitment ensures targeted lysis of the cancer cells recognised by the antibody of the present invention.

In a $3^{rd}$ implementation form, the effector group has a recognition specificity for the complement system and, in particular, for protein C1 or its truncated form C1q, which initiates the cascade of molecular events which result in the death of the targeted cell. Such a recruitment insures targeted lysis of the cancer cells recognised by the antibody of the present invention.

In a $4^{th}$ implementation form, the effector group exhibits a recognition specificity for the complement system and, in particular, for protein C3 or its truncated form C3b, thus ensuring recruitment of effector cells of the immune system, which cells induce the death of the targeted cell. Such a recruitment ensures targeted lysis of the cancer cells recognized by the antibody of the present invention.

The present invention relates to an antibody according to the present invention, a polynucleotide according to the present invention or a compound according to the present invention for use as a druger medicament.

Thus, the present invention relates to a pharmaceutical composition comprising, as an active ingredient, an antibody according to the present invention, or a polynucleotide according to the present invention or a compound according to the present invention and a pharmaceutically acceptable vehicle.

By "pharmaceutically acceptable vehicle", it is meant according to the present invention, any substance which is added to an antibody, polynucleotide or compound according to the present invention to promote its transport, avoid its substantial degradation in said composition and/or increase its half-life. Advantageously, such a pharmaceutically acceptable vehicle is sterile and nonpyrogenic. It is chosen depending on the type of application of the pharmaceutical composition of the invention and in particular as a function of its administration mode.

Thus, the pharmaceutical composition according to the invention consists of at least one antibody, or polynucleotide or compound according to the present invention in free form or in the form of an addition salt with a pharmaceutically acceptable acid, in pure state or in the form of a composition in which it is associated with any other pharmaceutically compatible product. The pharmaceutical compositions according to the invention can be employed by the systemic route; by the parenteral route, for example the intravenous, intra-arterial, intraperitoneal, intrathecal, intra-ventricular, intrasternal, intracranial, intramuscular or sub-cutaneous route; by topical route; by the oral route; by the rectal route; by the intranasal route or by inhalation.

As solid compositions for oral administration, tablets, pills, powders, etc. can be used where the antibody, polynucleotide or compound according to the invention is mixed with one or more conventionally used inert diluents, and possibly other substances such as, for example, a lubricant, a colorant, a coating etc.

As liquid compositions for oral or ocular administration pharmaceutically acceptable, suspensions, solutions, emulsions, syrups containing conventionally used inert diluents, and possibly other substances such as wetting products, sweeteners, thickeners, etc. can be used.

The sterile compositions for parenteral administration can be aqueous or non aqueous solutions, suspensions or emulsions. As a solvent or vehicle, water, propylene-glycol, plant oils or other suitable organic solvents can be used. These compositions can also contain adjuvants, such as wetting agents, isotonisers, emulsifiers, etc.

The compositions for topic administration can be for example creams, lotions, oral sprays, nose or eye drops or aerosol.

The daily dose level of the antibody, polynucleotide or compound according to the present invention is usually from 1 to 1 000 mg per adult (that is about 0.015 to 15 mg/kg), administrated in single or fractionated doses. These doses are given only by way of illustrating purposes. The physician, in any case, will be able to determine the most suitable real dose to a given individual patient and this dose varies depending on the patient's age, weight and response.

The present invention relates to an antibody according to the present invention, a polynucleotide according to the present invention, a compound according to the present invention or a pharmaceutical composition according to the present invention for use in the treatment and/or prevention of a disorder or condition involving a dysfunction, direct or in association with another physiological route, of the axis comprising an endothelin and at least one of its receptors such as, in particular, the endothelin receptor sub-type B.

Advantageously, such a disorder or such a condition is a cancer. As cancers, a melanoma, colon cancer, Kaposi's sarcoma, glioblastoma, ovary cancer and bladder cancer can be mentioned. Typically, this disorder is a melanoma or a glioblastoma.

Still in other words, the present invention relates to a process for treating and/or preventing a disorder or a condition involving a dysfunction, direct or in association with another physiological route, of the axis comprising an endothelin and at least one of its receptors such as, in particular, the endothelin receptor sub-type B in a patient having or likely to have such a disorder or such a condition. This process consists in administrating to said patient an efficient amount of an antibody according to the present invention, a polynucleotide according to the present invention, a compound according to the present invention or a pharmaceutical composition according to the present invention.

Finally, the present invention relates to the use of an antibody according to the present invention or a compound according to the present invention as a research tool particularly suitable for investigating signalling pathways associated with the endothelin/endothelin receptors axis, as well as for going forward in understanding structural and functional characteristics of these receptor family.

Further characteristics and advantages of the present invention will better appear to those skilled in the art upon reading examples given below by way of illustrating and non-limiting purposes, in reference to the appended figures.

BRIEF DESCRIPTION OF THE FIGURES

FIG. 4 shows images obtained in confocal microscopy on tumor cells from a biopsy of a patient having a glioblastoma in the presence of 1 µg/mL Rendomab-B36.

FIG. 5 shows the nucleic sequences deduced in amino acids from the variable domains of the light chain (VL) (FIG. 5A), in particular, VLRendoMabB49 (nucleic acid) that corresponds to SEQ ID NO: 36 and VLRendoMabB49 (amino acid) that corresponds to SEQ ID NO: 37, and the heavy chain (VH) (FIG. 5B), in particular, VHRendoMabB49 (nucleic acid) that corresponds to SEQ ID NO: 30 and VHRendoMabB49 (amino acid) that corresponds to SEQ ID NO: 31, of the IgG1/kappa murine antibody Rendomab-B49 specific to the endothelin receptor B.

FIG. 6 shows the nucleic sequences deduced in amino acids from the variable domains of the light chain (VL) (FIG. 6A), in particular, VLRendoMabB41 (nucleic acid) that corresponds to SEQ ID NO: 38 and VLRendoMabB41 (amino acid) that corresponds to SEQ ID NO: 39, and the heavy chain (VH) (FIG. 6B), in particular, VHRendoMabB41 (nucleic acid) that corresponds to SEQ ID NO: 32 and VHRendoMabB41 (amino acid) that corresponds to SEQ ID NO: 33, of the IgG1/kappa murine antibody Rendomab-B41 specific to the endothelin receptor B.

FIG. 7 shows the nucleic sequences deduced in amino acids of the variable domains of the light chain (VL) (FIG. 7A), in particular, VLRendoMabB36 (nucleic acid) that corresponds to SEQ ID NO: 40 and VLRendoMabB36 (amino acid) that corresponds to SEQ ID NO: 41, and the heavy chain (VH) (FIG. 7B), in particular, VHRendoMabB36 (nucleic acid) that corresponds to SEQ ID NO: 34 and VHRendoMabB36 (amino acid) that corresponds to SEQ ID NO: 35, of the IgG3/kappa murine antibody Rendomab-B36 specific to the endothelin receptor B.

FIG. 8 shows the epitopic mapping. FIG. 8A presents the revealed "Pep scan" membrane. FIG. 8B presents the sequences of the peptides recognized by Rendomab-B49 that corresponds to SEQ ID NO: 42 with high intensity (C5, C6, C7, C8, C9 and C10 peptides). FIG. 8C presents the location of the epitope recognized by Rendomab-B49 in the sequence of the human endothelin receptor sub-type B.

DETAILED DISCLOSURE OF PARTICULAR EMBODIMENTS

I. Materials and Methods

I.1. Immunisation

Figure 1A:
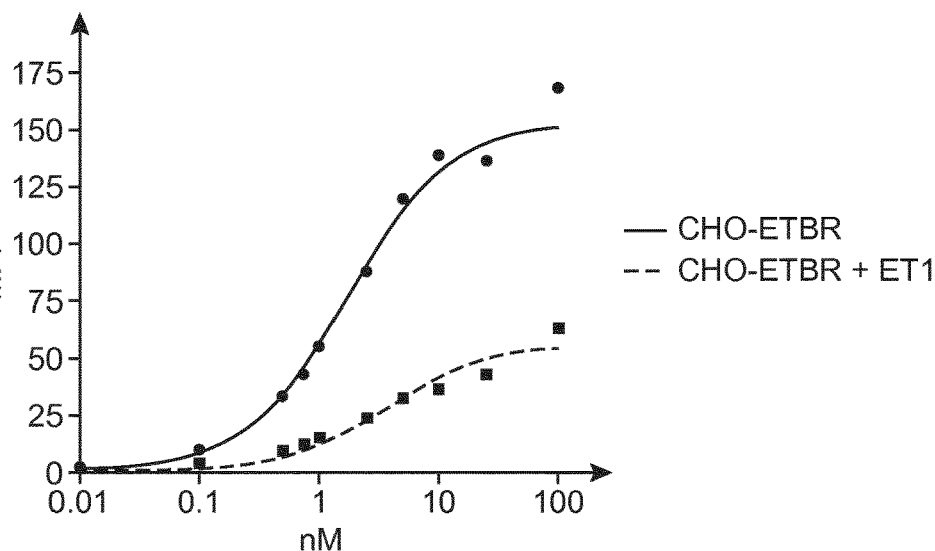
FIG. 1 shows binding curves of Rendomab-B49 (FIG. 1A), Rendomab-B41 (FIG. 1B) and Rendomab-B36 (FIG. 1C) on CHO cells overexpressing ETB-R with (squares) or without (dots) pre-incubation of the cells in the presence of 300 nM of endothelin 1. In both cases, an affinity in the order of one nanomole has been measured.

The so-called "gene immunisation" strategy developed in the laboratory of the inventors consists in combining DNA injections with protein boosts as an injection of cells overexpressing ETB-R (Allard et al, 2011, "Electroporation-aided DNA immunisation generates polyclonal antibodies against the native conformation of human endothelin B receptor", DNA and Cell Biology, vol. 30, pages 727-737).

Briefly, three injections, in a mouse tibial muscle, of 50 µg of plasmid DNA pcDNA3/ETB-R, were made with a periodicity of 14 days. Each DNA injection was followed by an electrostimulation according to the following characteristics: 8 pulses each of 20 ms, 80 Volts, 1 Hz. Three immunisation boosts were then made, by injection by the intra-peritoneal route of $2.10^6$ COS cells transiently overexpressing ETB-R.

The best responder mice were sacrificed in order to conduct cell fusion of the lymphoid cells of their spleens with the murine myeloma NS-1.

I.2. Screening Hybridomas

The hybridomas obtained were first screened by ELISA on CHO cells stably expressing ETB-R, with as a negative control, CHO cells expressing the irrelevant receptor NK1 (CHO-WT).

The hybridomas retained were then screened in flow cytometry (apparatus Guava, Millipore). Three hybridomas called "Rendomab-B49", "Rendomab-B41" and "Rendomab-B36" were finally retained at the end of both these screens. The antibodies secreted were then produced from liquid tumors (ascites) induced in the mouse by injection by the intra-peritoneal route of the selected hybridomas.

II. Biochemical Characterisation

After purifying Rendomab-B49, Rendomab-B41 and Rendomab-B36, the characterisation of their biochemical properties was conducted.

The isotyping of the heavy and light chains of Rendomab-B49 was made using the "Rapid ELISA Mouse mAb Isotyping" kit from Piercell. It is an immunoglobulin of isotype 1, G type, for the heavy chain and kappa for the light chain.

Rendomab-B49 is thus an IgG1/kappa type immunoglobulin. Rendomab-B41 and Rendomab-B36 are, an IgG1/kappa type immunoglobulin and an IgG3/kappa type immunoglobulin, respectively.

After purifying Rendomab-B49, Rendomab-B41 and Rendomab-B36, their binding specificity was established by flow cytometry (Facs Calibur, Becton Dickinson BD Bioscience), by indirect labelling using a commercial fluorescent anti-mouse secondary antibody (Life Technologie: Alexa Fluor® 488 F(ab')2 fragment of goat anti-mouse IgG (H+L)*2 mg/mL*).

CHO-ETBR cells were separated into 2 groups. One of the groups was incubated beforehand in a culture medium for 2 h at 37° C. in the presence of endothelin 1 at a final concentration of 300 nM so as to internalise the ETBR receptor for the purpose of demonstrating the recognition specificity of the 3 Rendomab antibodies to ETB-R.

Then, the cells were aliquoted in a 15 ml falcon tube (300 000 cells/tube) in the presence of an increasing concentration (concentration range from 0.04 nM to 800 nM two by two) of antibody Rendomab-B49. After 2 h incubation at 4° C., the cells are washed three times in a PBS buffer and then incubated for 1 h at 4° C. with the secondary antibody at a final concentration of 4 µg/mL. The cells are then washed 3 times with a PBS buffer and then analyzed with FACs Calibur after counting 30 000 cells.

III. Binding Properties on Glioblastoma Cells

III.1. Protocol

The cells are cultured either in neurospheres (suspended culture) or in adherence on glass slides covered with poly D Lysine/Laminine. The cells are then bound by a 4% paraformaldehyde solution for 15 min at room temperature, and then washed twice with PBS (SigmaAldrich). The non-specific sites are blocked and the cells are permeabilized by a PBS solution+5% donkey serum+0.1% Triton, for 30 min.

The primary antibody Rendomab-B49, diluted in the previous solution at 1 µg/mL is contacted with the cells overnight at 8° C. After 2 rinses with PBS, the cells are incubated with a commercial secondary antibody at a final concentration of 4 µg/ml either coupled with Alexa 488 (Life Technologie: Alexa Fluor® 488 F(ab')2 fragment of goat anti-mouse IgG (H+L)*2 mg/mL*) or coupled with Alexa 680 (Life Technologie Alexa Fluor® 680 F(ab')2 fragment of goat anti-mouse IgG (H+L)*2 mg/mL*) for 2 h according to the recommendations of the provider, and then rinsed twice with PBS.

The cells are briefly incubated with a 1 µg/ml DAPI (4',6-diamidino-2-phenylindole) solution to view the nuclei, and then after washing with PBS, the coverslips are mounted between slip and slide with an ad hoc assembling medium for observation. The photographs are taken with a Zeiss microscope provided with a 400 magnification apotome module.

III.2. Results

Figure 1B:
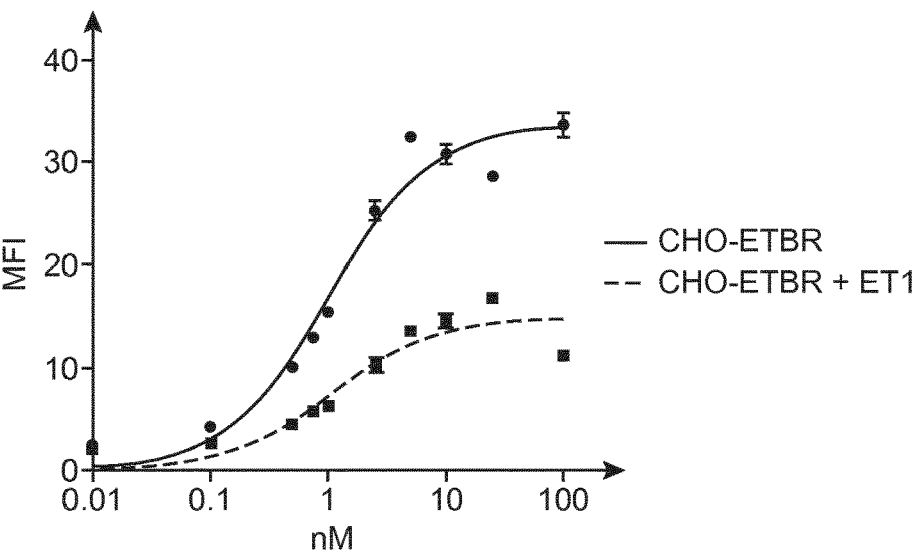
Figure 1C:
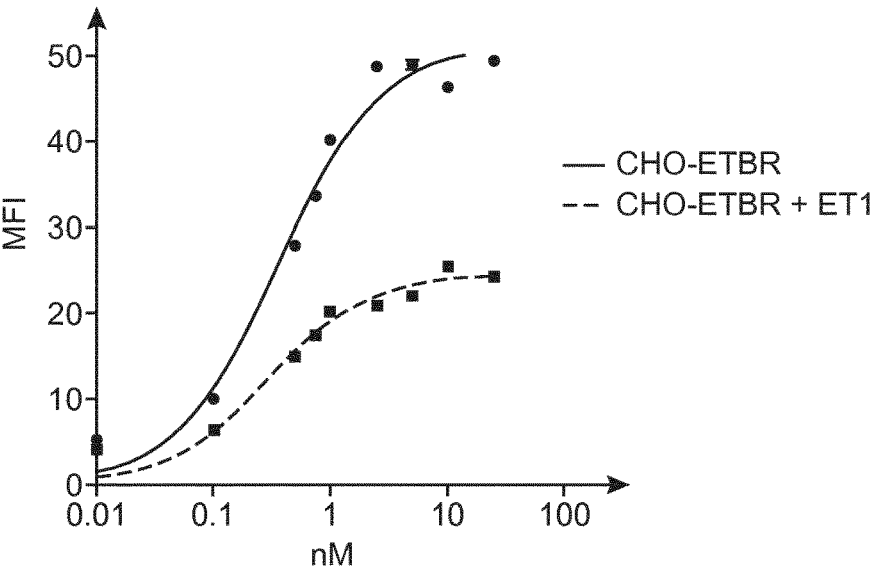

The affinity close to the nanomolar range for Rendomab-B49, Rendomab-B41 and Rendomab-B36 and their exclusive specificity for the human endothelin receptor sub-type B are illustrated in FIG. 1.

The binding curve observed for Rendomab-B49 (FIG. 1A), Rendomab-B41 (FIG. 1B) and Rendomab-B36 (FIG. 1C) is characteristic of the binding of an antibody to its target with a saturation plateau.

In addition, the pre-incubation of CHO-ETBR cells for 2 h at 37° C. in the presence of 300 nM of endothelin 1 causes the internalisation of ETB-R, which results in a drop of more than 50% of the Rendomab-B49, Rendomab-B41 and Rendomab-B36 binding under these conditions thus demonstrating the binding specificity of these antibodies for ETB-R. The apparent dissociation constant $K_D$ of the antibodies is determined by taking the value of the concentration giving a MFI equal to 50% the value of the MFI at the plateau. This constant is close to 1 nM for the 3 antibodies.

Then, the absence of binding of Rendomab-B49, Rendomab-B41 and Rendomab-B36 on CHO-WT cells non transfected by ETBR is noted showing that the binding observed on CHO-ETBR cells is not due to a membrane protein of the CHO cells.

Binding experiments on tumor cells isolated from biopsies of patients with a glioblastoma.

Figure 2A:
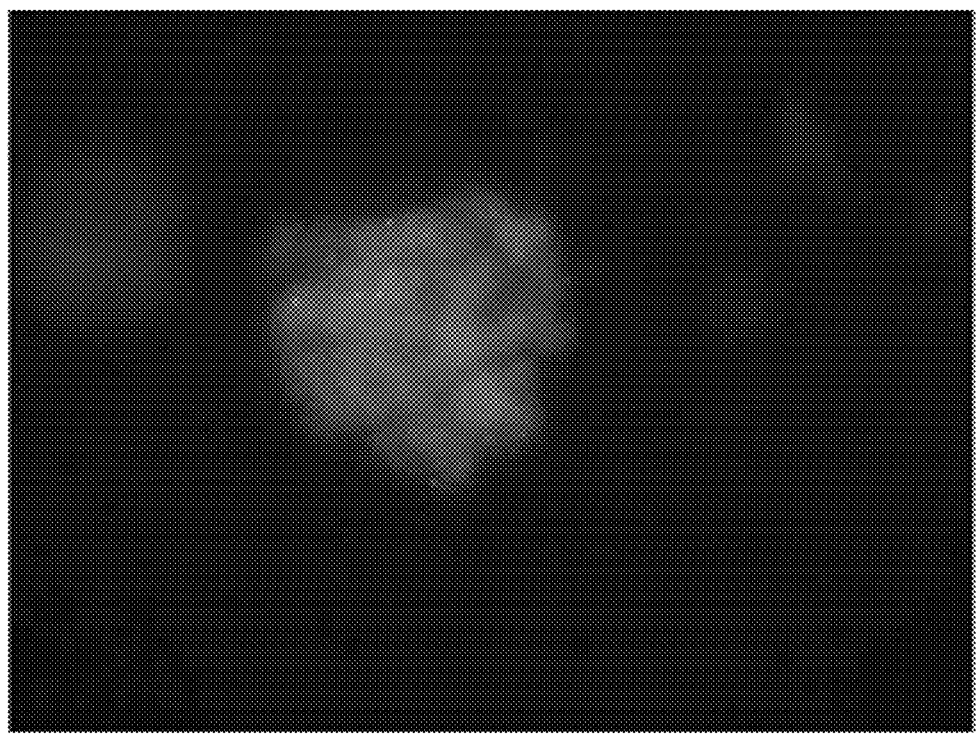
FIG. 2 shows images obtained in confocal microscopy on neurospheres from a biopsy of a patient having a high grade glioblastoma in the presence of 1 µg/mL of labelled Rendomab-B1 (FIG. 2A) or 1 µg/mL of labelled Rendomab-B49 (FIG. 2B). Only the nuclei of DAPI labelled cells are viewed in FIG. 2A.
Figure 2B:
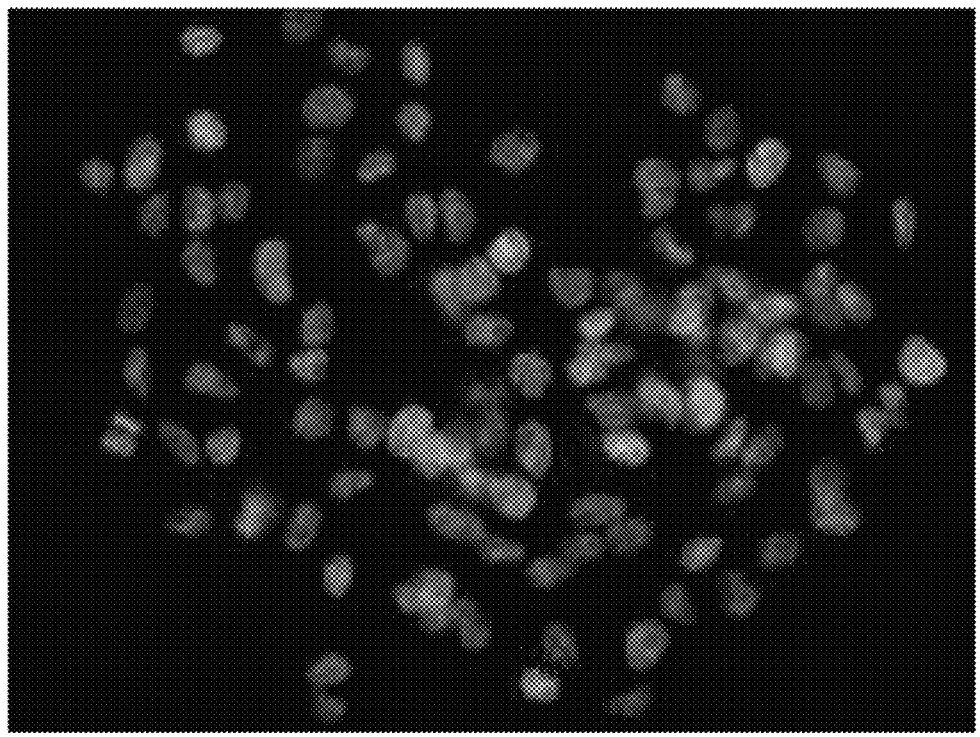

In FIG. 2, there is an absence of labelling of neurospheres isolated from a high grade glioblastoma tumor with the antibody Rendomab-B1 (FIG. 2A) whereas it is observed, on the same cells, a very strong fluorescent labelling with the antibody Rendomab-B49 (FIG. 2B).

Figure 3A:
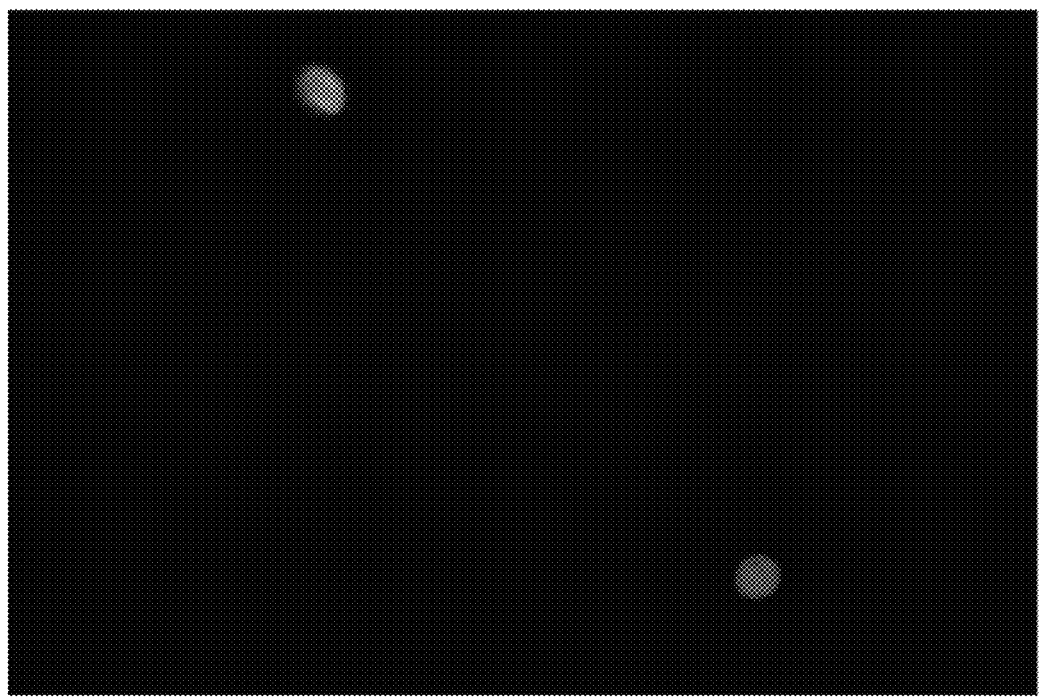
FIG. 3 shows images obtained in confocal microscopy on tumor cells from a biopsy of a patient having a low grade glioblastoma in the presence of DAPI (FIG. 3A) or 1 µg/mL of Rendomab-B49 (FIG. 3B).
Figure 3B:
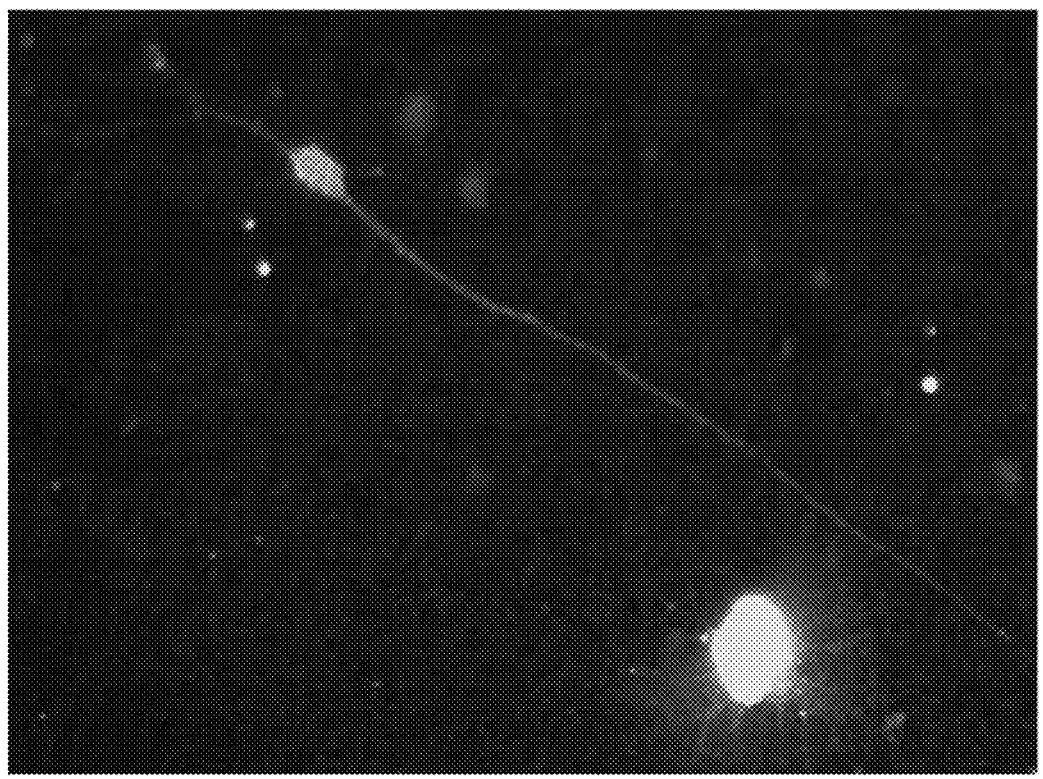

Likewise, FIG. 3 shows a strong fluorescent labelling by the antibody Rendomab-B49 (FIG. 3B) of tumor cells isolated from a low grade glioblastoma tumor, these cells being also labelled with DAPI (FIG. 3A).

Comparable results are obtained with the antibodies Rendomab-B41 and Rendomab-B36. To that end, FIG. 4 shows a strong fluorescent labelling with the antibody Rendomab-B36 on tumor cells isolated from a glioblastoma tumor.

IV. Molecular Cloning

The cloning of nucleic precursors coding the heavy chain and the light chain of Rendomab-B1 was made using the kits: "Gene-Elute/total RNA" (Sigma) and "RACE-PCR" (Invitrogen).

The nucleic sequences deduced in amino acids of the variable domains of the light chain (VL) and the heavy chain (VH) of Rendomab-B49, Rendomab-B41 and Rendomab-B36 are given in FIGS. 5 to 7 respectively.

V. Epitopic Mapping

V.1. Materials and Methods

The mapping of the epitope recognised by Rendomab-B49, Rendomab-B41 and Rendomab-B36 at the ETB-R surface was made by a "Pep-scan" technique in collaboration with and according to the protocols developed within UMR 3145 "SysDiag" CNRS/BioRad located in Montpellier (Dr. Claude Granier). The sequence of the human endothelin receptor sub-type B exhibits the following amino acid sequence:

```
                                        (SEQ ID NO: 42)
MQPPPSLCGRALVALVLACGLSRIWGEERGFPPDRATPLLQTAEIMTPPT

KTLWPKGSNASLARSLAPAEVPKGDRTAGSPPRTISPPPCQGPIEIKETF

KYINTVVSCLVFVLGIIGNSTLLRIIYKNKCMRNGPNILIASLALGDLLH

IVIDIPINVYKLLAEDWPFGAEMCKLVPFIQKASVGITVLSLCALSIDRY

RAVASWSRIKGIGVPKWTAVEIVLIWVVSVVLAVPEAIGFDIITMDYKGS

YLRICLLHPVQKTAFMQFYKTAKDWWLFSFYFCLPLAITAFFYTLMTCEM

LRKKSGMQIALNDHLKORREVAKTVFCLVLVFALCWLPLHLSRILKLTLY

NQNDPNRCELLSFLLVLDYIGINMASLNSCINPIALYLVSKRFKNCFKSC

LCCWCQSFEEKQSLEEKQSCLKFKANDHGYDNFRSSNKYSSS.
```

For this, 144 peptides of the 12 amino acids each offset by one amino acid were used. These peptides correspond to all the ETB-R sequences displayed on the extra-cytoplasmic side of the membrane.

In order to reveal the epitopic peptide(s) recognized by Rendomab-B49, the "Pep-scan" membrane was treated according to the following protocol:

humidification of the membrane in an ethanol bath;
3 washes in 25 ml of TBS buffer (50 mM Tris, 150 mM NaCl, pH 7.4) for 10 min under agitation at ambient temperature;
saturation of the membrane with 25 ml of the saturation buffer (TBS, 5% skimmed milk powder, 0.1% Tween 20) for 30 min under agitation at ambient temperature;
incubation with 25 ml of saturation buffer containing the Rendomab-B49 antibody at a final concentration of 1 µg/ml overnight at 4° C. under agitation;
3 short washes (30 seconds) with TBS buffer then 3 washes of 10 min under agitation with 25 ml of TBST buffer (TBST=TBS+0.1% Tween 20);
incubation with 25 ml of saturation buffer containing the goat anti-mouse secondary antibody diluted at 1/5,000 for 30 min at ambient temperature under agitation;
3 short washes (30 seconds) with TBS buffer then 3 washes of 10 min under agitation with 25 ml of TBST buffer;
revelation of the membrane by immersing it in the revelation solution from Pierce (Pierce ECL Plus Western Blotting Ref: 32132) for 5 min and by the signal acquisition in automatic mode by the system Chemi-Doc™ of BioRad).

V.2. Results

The results of the epitopic analysis of Rendomab-B49 are presented at FIG. 8. The peptide sequences hybridizing with high intensity are C5, C6, C7, C8, C9 and C10 peptides (FIG. 8A).

Their alignment makes it possible to identify the epitope predominantly recognized by Rendomab-B49: the latter is EVPKGDR corresponding to the sequence from amino acid 70 to amino acid 76 in SEQ ID NO: 42 (FIG. 8B). As soon as the glutamic acid E70 is lacking in peptide C11 of sequence VPKGDRTAGSPP corresponding to the sequence from amino acid 71 to amino acid 82 in SEQ ID NO: 42, the antibody binding decreases significantly (FIG. 8A).

The location of the epitopic peptide in the sequence of the human endothelin receptor sub-type B is presented at FIG. 8C. This sequence is at the N-terminal end of the receptor.

What is claimed is:

1. An antibody directed against an endothelin receptor sub-type B comprising:
a heavy chain variable region comprising
    a CDR1 (hereinafter designated CDR1$_H$) the amino acid sequence of which is GYTFISYW (SEQ ID NO: 5);
    a CDR2 (hereinafter designated CDR2$_H$) the amino acid sequence of which is IDPDSGGT (SEQ ID NO: 10); and
    a CDR3 (hereinafter designated CDR3$_H$) the amino acid sequence of which is AREGDYAWFAY (SEQ ID NO: 15); and
a light chain variable region comprising
    a CDR1 (hereinafter designated CDR1$_L$) the amino acid sequence of which is QSIVHSNGNTY (SEQ ID NO: 22);
    a CDR2 (hereinafter designated CDR2$_L$) the amino acid sequence of which is KVS; and
    a CDR3 (hereinafter designated CDR3$_L$) the amino acid sequence of which is FQGSHVPWT (SEQ ID NO: 27);
or
ii) a heavy chain variable region comprising
    a CDR1$_H$ the amnio acid sequence of which is GYTFTSYW (SEQ ID NO: 7);
    a CDR2$_H$ the amnio acid sequence of which is IDPDSGGT (SEQ ID NO: 10); and
    a CDR3$_H$ the amnio acid sequence of which is VREGWDAWFVY (SEQ ID NO: 17); and
a light chain variable region comprising
    a CDR1$_L$ the amnio acid sequence of which is QSIVHSNGNTY (SEQ ID NO: 22);
    a CDR2$_L$ the amnio acid sequence of which is KVF; and
    a CDR3$_L$ the amnio acid sequence of which is FQGSHVPLT (SEQ ID NO: 29); or iii) a heavy chain variable region comprising
    a CDR1$_H$ the amnio acid sequence of which is GYTFTSYW (SEQ ID NO: 7);
    a CDR2$_H$ the amnio acid sequence of which is IDPNSGGT (SEQ ID NO: 12); and
    a CDR3$_H$ the amnio acid sequence of which is AREGEFAWFAY (SEQ ID NO: 19); and
a light chain variable region comprising
    a CDR1$_L$ the amnio acid sequence of which is QNIVHSNGNTY (SEQ ID NO: 24);
    a CDR2$_L$ the amnio acid sequence of which is KVS; and
    a CDR3$_L$ the amnio acid sequence of which is FQGSHVPLT (SEQ ID NO: 29);
a fragment or derivative thereof,
wherein said fragment has at least one antigen-binding site,
wherein said derivative is a single chain Fv or a single domain antibody, and
wherein said antibody and said fragment or derivative thereof are capable of recognising particular conformational isomers of the endothelin receptor sub-type B expressed at the surface of glioblastoma cells.

2. The antibody according to claim 1, wherein said antibody comprises a heavy chain variable region the amino acid sequence of which exhibits at least 80% identity with the following sequence:

(SEQ ID NO: 31)
QVQLQQPGAALVKPGASVKLSCKASGYTFISYWMLWVKQRPGRGLEWIG

RIDPDSGGTKYNEKFKSKATLTVDKSSSTAYMQLSSLTSEDSAVYYCAR

EGDYAWFAYWGQGTLVPVSA.

3. The antibody according to claim 1, wherein said antibody comprises a light chain variable region the amino acid sequence of which exhibits at least 80% identity with the following sequence:

```
                                                  (SEQ ID NO: 37)
DVLMTQTPLSLPVSLGDQASISCRSSQSIVHSNGNTYLEWYLQKPGQSPK
LLIYKVSNRFSGVPDRFSGSGSGTDFTLKISRVEAEDLGVYYC**FQGSHVP
WTF**GGGTKLEIK.
```

4. The antibody according to claim 1, wherein said antibody is an IgG1/kappa type or IgG3/kappa type immunoglobulin.

5. The antibody according to claim 1, wherein said antibody is monoclonal.

6. The antibody according to claim 1, wherein said antibody is a monoclonal murine antibody obtained from a hybridoma chosen from a hybridoma deposited with CNCM on the 19 May 2016 under accession number CNCM I-5084, a hybridoma deposited with the CNCM on the 7 Jun. 2016 under accession number CNCM I-5104 and a hybridoma deposited with the CNCM on the 7 Jun. 2016 under accession number CNCM I-5103.

7. The antibody according to claim 1, wherein said antibody is a chimerized antibody.

8. The antibody according to claim 1, wherein said antibody is a humanized antibody.

9. A pharmaceutical composition comprising, as an active ingredient, an antibody according to claim 1 and a pharmaceutically acceptable vehicle.

10. A compound comprising an antibody according to claim 1 conjugated with an element chosen from the group consisting of a cytotoxic group, an easily detectable group, or an effector group,
  wherein the cytotoxic group is selected from the group consisting of alkylating agents, methotrexate, 5-fluorouraci, vinblastine, gemcitabine, fludarabine, nicotinamide, doxorubicin, mitomycin, L-asparaginase, cisplatin, taxol and analogues/derivatives thereof, ricin, abrin, Pseudomonas exotoxin, TNF-alpha, interleukin 2, methotrexate-alanine, mitomycin phosphate, 5-fluorocytosine, photofrin, capecitabine, a carboxypeptidase, an aminopeptidase or endopeptidase, phosphatase, a sulphatase, an amidase, a kinase, a glycosidase, a deaminase, a reductase, an oxidase, an anti-sense oligonucleotide and an aptamer;
  wherein the easily detectable group is selected in the group consisting of biotin, digoxigenin, 5-bromodeoxiuridin, an alkaline phosphatase, a peroxidase, an acetylcholine esterase (AChE), a glucose amylase, a lysozyme, fluorescein and derivatives thereof, rhodamine and derivatives thereof, GFP (Green Fluorescent Protein) and derivatives thereof and umbelliferone; luminol; luciferase and luciferin; iodine-123, iodine-125, iodine-126, iodine-133, indium-Ill, indium-113m, bromine-77, gallium-67, gallium-68, ruthenium-95, ruthenium-97, technetium-99m, fluorine-19, fluorine-18, carbon-13, nitrogen-15, oxygen-17, scandium-47, tellurium-122m, thulium-165 and yttrium-199; and
  wherein the effector group is selected from the group consisting of a ligand of a cancer marker, an antibody identical to or different from the antibody according to claim 1, a protein, a peptide, a DNA, an RNA, an RNAi, an aptamer, a PNA and an LNA.

11. A pharmaceutical composition comprising, as an active ingredient, a compound according to claim 10 and a pharmaceutically acceptable vehicle.

12. A process for diagnosing a glioblastoma in vitro comprising the steps of:
  $a_1'$) contacting a biological sample taken from a subject with a compound according to claim 10;
  $b_1'$) detecting the signal emitted by the easily detectable group and
  $c_1'$) determining the presence or absence of a glioblastoma in said subject based on the signal detected in step ($b_1'$).

13. An antibody directed against the endothelin receptor sub-type B comprising:
  i) a heavy chain variable region comprising
    a CDR1 (hereinafter designated CDR1H) the amino acid sequence of which is GYTFISYW (SEQ ID NO: 5);
    a CDR2 (hereinafter designated CDR2H) the amino acid sequence of which is IDPDSGGT (SEQ ID NO: 10); and
    a CDR3 (hereinafter designated CDR3H) the amino acid sequence of which is AREGDYAWFAY (SEQ ID NO: 15); and
  a light chain variable region comprising
    a CDR1 (hereinafter designated CDR1L) the amino acid sequence of which is QSIVHSNGNTY (SEQ ID NO: 22);
    a CDR2 (hereinafter designated CDR2L) the amino acid sequence of which is KVS; and
    a CDR3 (hereinafter designated CDR3L) the amino acid sequence of which is FQGSHVPWT (SEQ ID NO: 27);
  or
  ii) a heavy chain variable region comprising
    a CDR1H the amino acid sequence of which is GYTFTSYW (SEQ ID NO: 7);
    a CDR2H the amino acid sequence of which is IDPDSGGT (SEQ ID NO: 10); and
    a CDR3H the amino acid sequence of which is VREGWDAWFVY (SEQ ID NO: 17); and
  a light chain variable region comprising
    a CDR1L the amino acid sequence of which is QSIVHSNGNTY (SEQ ID NO: 22);
    a CDR2L the amino acid sequence of which is KVF; and
    a CDR3L the amino acid sequence of which is FQGSHVPLT (SEQ ID NO: 29);
  or
  iii) a heavy chain variable region comprising
    a CDR1H the amino acid sequence of which is GYTFTSYW (SEQ ID NO: 7);
    a CDR2H the amino acid sequence of which is IDPNSGGT (SEQ ID NO: 12); and
    a CDR3H the amino acid sequence of which is AREGEFAWFAY (SEQ ID NO: 19) and
  a light chain variable region comprising
    a CDR1L the amino acid sequence of which is QNIVHSNGYTY (SEQ ID NO: 24);
    a CDR2L the amino acid sequence of which is KVS; and
    a CDR3L the amino acid sequence of which is FQGSHVPLT (SEQ ID NO: 29);
  a fragment or derivative thereof,
  wherein said fragment has at least one antigen-binding site, and wherein said derivative is a single chain Fv or a single domain antibody.

14. A compound comprising the antibody according to claim 13, conjugated with a cytotoxic group or an effector group wherein an effector group is selected from the group consisting of a ligand of a cancer marker; an antibody identical to or different from the antibody according to claim 1; a protein; a peptide; a DNA, an RNA, an RNAi, an aptamer, a PNA and an LNA.

15. The antibody according to claim 13, wherein the amino acid sequence of the heavy chain variable region exhibits at least 80% identity with sequence:

(SEQ ID NO: 31)
QVQLQQPGAALVKPGASVKLSCKASGYTFISYWMLWVKQRPGRGLEWIG

RIDPDSGGTKYNEKFKSKATLTVDKSSSTAYMQLSSLTSEDSAVYYCAR

EGDYAWFAYWGQGTLVPVSA;

and/or
wherein the amino acid sequence of the light chain variable region exhibits at least 80% identity with sequence:

(SEQ ID NO: 37)
DVLMTQTPLSLPVSLGDQASISCRSSQSIVHSNGNTYLEWYLQKPGQSPK
LLIYKVSNRFSGVPDRFSGSGSGTDFTLKISRVEAEDLGVYYC**FQGSHVP
WT**FGGGTKLEIK.

16. A compound comprising the antibody according to claim 15, conjugated with a cytotoxic group or an effector group wherein an effector group is selected from the group consisting of a ligand of a cancer marker; an antibody identical to or different from the antibody according to claim 1; a protein; a peptide; a DNA, an RNA, an RNAi, an aptamer, a PNA and an LNA.

17. A method for treating a cancer associated with ETBR overexpression, which method comprises administering to a subject in need thereof a compound comprising an antibody against endothelin receptor sub-type B, or an antigen-binding fragment thereof or derivative thereof, wherein antibody against endothelin receptor sub-type B, antigen-binding fragment thereof or derivative thereof, is conjugated with a cytotoxic group, and wherein the antibody against endothelin receptor sub-type B comprises:
  i) a heavy chain variable region comprising
    a CDR1 (hereinafter designated CDR1H) the amino acid sequence of which is GYTFISYW (SEQ ID NO: 5);
    a CDR2 (hereinafter designated CDR2H) the amino acid sequence of which is IDPDSGGT (SEQ ID NO: 10); and
    a CDR3 (hereinafter designated CDR3H) the amino acid sequence of which is AREGDYAWFAY (SEQ ID NO: 15);
  and
  a light chain variable region comprising
    a CDR1 (hereinafter designated CDR1L) the amino acid sequence of which is QSIVHSNGNTY (SEQ ID NO: 22);
    a CDR2 (hereinafter designated CDR2L) the amino acid sequence of which is KVS; and
    a CDR3 (hereinafter designated CDR3L) the amino acid sequence of which is FQGSHVPWT (SEQ ID NO: 27);
or
  ii) a heavy chain variable region comprising
    a CDR1H the amino acid sequence of which is GYTFTSYW (SEQ ID NO: 7);
    a CDR2H the amino acid sequence of which is IDPDSGGT (SEQ ID NO: 10); and
    a CDR3H the amino acid sequence of which is VREGWDAWFVY (SEQ ID NO: 17); and
  a light chain variable region comprising
    a CDR1L the amino acid sequence of which is QSIVHSNGNTY (SEQ ID NO: 22);
    a CDR2L the amino acid sequence of which is KVF; and
    a CDR3L the amino acid sequence of which is FQGSHVPLT (SEQ ID NO: 29);
or
  iii) a heavy chain variable region comprising
    a CDR1H the amino acid sequence of which is GYTFTSYW (SEQ ID NO: 7);
    a CDR2H the amino acid sequence of which is IDPNSGGT (SEQ ID NO: 12); and
    a CDR3H the amino acid sequence of which is AREGEFAWFAY (SEQ ID NO: 19) and
  a light chain variable region comprising
    a CDR1L the amino acid sequence of which is QNIVHSNGYTY (SEQ ID NO: 24);
    a CDR2L the amino acid sequence of which is KVS; and
    a CDR3L the amino acid sequence of which is FQGSHVPLT (SEQ ID NO: 29), wherein said derivative is a single chain Fv or a single domain antibody.

18. The method according to claim 17, wherein said cancer is a melanoma, glioblastoma, or bladder cancer.

19. The method according to claim 17, wherein said cancer is a melanoma.

20. The method according to claim 17, wherein said cancer is a glioblastoma.

21. The method according to claim 17, wherein said antibody against endothelin receptor sub-type B, the amino acid sequence of the heavy chain variable region exhibits at least 80% identity with sequence:
QVQLQQPGAALVKPGASVKLSCKASGYTFI-SYWMLWVKQRPGRGLEWIGRIDPDSGGTKY NEKFKSKATLTVDKSSSTAYMQLSSLTSEDSAVYY-CAREGDYAWFAYWGQGTLVPVSA (SEQ ID NO: 31);
and/or
the amino acid sequence of the light chain variable region exhibits at least 80% identity with sequence:

(SEQ ID NO: 37)
DVLMTQTPLSLPVSLGDQASISCRSSQSIVHSNGNTYLEWYLQKPGQSPK
LLIYKVSNRFSGVPDRFSGSGSGTDFTLKISRVEAEDLGVYYC**FQGSHVP
WT**FGGGTKLEIK.

* * * * *